United States Patent
West et al.

(10) Patent No.: US 12,168,226 B2
(45) Date of Patent: Dec. 17, 2024

(54) HIGH RESOLUTION SPATIAL GENOMIC ANALYSIS OF TISSUES AND CELL AGGREGATES

(71) Applicant: BioSkryb Genomics, Inc., Durham, NC (US)

(72) Inventors: Jason A. A. West, Chapel Hill, NC (US); Kyle Hukari, Foster City, CA (US)

(73) Assignee: BioSkryb Genomics, Inc., Durham, NC (US)

( * ) Notice: Subject to any disclaimer, the term of this patent is extended or adjusted under 35 U.S.C. 154(b) by 705 days.

(21) Appl. No.: 16/342,758

(22) PCT Filed: Oct. 17, 2017

(86) PCT No.: PCT/US2017/056865
§ 371 (c)(1),
(2) Date: Apr. 17, 2019

(87) PCT Pub. No.: WO2018/075436
PCT Pub. Date: Apr. 26, 2018

(65) Prior Publication Data
US 2019/0262831 A1 Aug. 29, 2019

(51) Int. Cl.
| | | |
|---|---|---|
| *C12Q 1/6816* | (2018.01) | |
| *B01L 3/00* | (2006.01) | |
| *C12Q 1/68* | (2018.01) | |
| *C12Q 1/6851* | (2018.01) | |
| *C12Q 1/6853* | (2018.01) | |
| *C40B 20/02* | (2006.01) | |
| *C40B 20/04* | (2006.01) | |
| *C40B 40/06* | (2006.01) | |
| *C40B 40/10* | (2006.01) | |
| *B01L 7/00* | (2006.01) | |

(52) U.S. Cl.
CPC ....... B01L 3/502715 (2013.01); B01L 3/5027 (2013.01); B01L 3/502753 (2013.01); C12Q 1/68 (2013.01); C12Q 1/6816 (2013.01); C12Q 1/6851 (2013.01); C12Q 1/6853 (2013.01); C40B 20/02 (2013.01); C40B 20/04 (2013.01); C40B 40/06 (2013.01); C40B 40/10 (2013.01); *B01L 7/525* (2013.01); *B01L 2200/0647* (2013.01); *B01L 2300/021* (2013.01); *B01L 2300/0645* (2013.01); *B01L 2300/0681* (2013.01); *B01L 2300/0819* (2013.01); *B01L 2300/0861* (2013.01); *B01L 2300/0887* (2013.01); *B01L 2300/1827* (2013.01); *B01L 2400/0421* (2013.01)

(58) Field of Classification Search
None
See application file for complete search history.

(56) References Cited

U.S. PATENT DOCUMENTS

| | | | |
|---|---|---|---|
| 2005/0123951 A1* | 6/2005 | Paek | C12Q 1/6837 435/6 |
| 2012/0245053 A1* | 9/2012 | Shirai | C40B 40/08 506/9 |
| 2013/0053256 A1* | 2/2013 | Hubbell | C40B 70/00 506/4 |
| 2013/0116128 A1* | 5/2013 | Shen | C12Q 1/6874 506/2 |
| 2014/0066318 A1* | 3/2014 | Frisen et al. | C12Q 1/68 |
| 2016/0145677 A1 | 5/2016 | Chee et al. | |

FOREIGN PATENT DOCUMENTS

| | | | | |
|---|---|---|---|---|
| CA | 2473308 | * | 8/2002 | C12Q 1/68 |
| WO | WO 2012/140224 A1 | | 10/2012 | |
| WO | WO 2017/019456 A2 | | 2/2017 | |

OTHER PUBLICATIONS

Hrdlickova et al.; "RNA-Seq methods for transcriptome analysis"; Wiley Periodicals WIREs RNA; 2016; 17 pages.

Fuller et al.; "The challenges of sequencing by synthesis"; Nature Biotechnology; vol. 27; Nov. 2009; p. 1013-1023 plus two pages.

Shalek et al.; "Single cell RNA Seq reveals dynamic paracrine control of cellular variation"; Nature; vol. 510; Jun. 2014; p. 363-369.

Pollen et al.; "Low-coverage single-cell mRNA sequencing reveals cellular heterogeneity and activated signaling pathways in developing cerebral cortex"; Nature Biotechnology; vol. 32; 2014; 46 pages.

Pollen et al.; "Molecular Identity of Human Outer Radial Glia during Cortical Development"; Cell; vol. 163; Sep. 2015; p. 55-67.

Gawad et al.; "Dissecting the clonal origins of childhood acute lymphoblastic leukemia by single-cell genomics"; PNAS; vol. 111; Dec. 2014; p. 17947-17952.

Gong et al.; "Simple Method to Prepare Oligonucleotide-Conjugated Antibodies and Its Application in Multiplex Protein Detection in Single Cells"; Bioconjugate Chemistry; vol. 27; 2016; p. 217-225.

Genschaft et al.; "Multiplexed, targeted profiling of single-cell proteomes and transcriptomes in a single reaction"; Genome Biology; vol. 17; 2016; 15 pages.

Crosetto et al.; "Spatially resolved transcriptomics and beyond"; Nature Reviews Genetics; vol. 16; Jan. 2015; p. 57-66.

Jiang et al.; "High-Throughput Single-Cell Cultivation on Microfluidic Streak Plates"; Applied and Environmental Microbiology; vol. 82; Apr. 2016; p. 2210-2218.

Macosko et al.; "Highly Parallel Genome-wide Expression Profiling of Individual Cells Using Nanoliter Droplets"; Cell; vol. 161; 2015; p. 1202-1214.

(Continued)

*Primary Examiner* — Katherine D Salmon
(74) *Attorney, Agent, or Firm* — Wilson Sonsini Goodrich & Rosati

(57) ABSTRACT

Provided are devices and methods for capturing template sample nucleic acids in a spatially specific manner that is coordinated with the original location of the templates in a tissue sample. By preserving spatial information regarding a given sample, the disclosed technology allows for improved diagnostics as well as improved therapeutic decision making for patient care and therapy.

12 Claims, 9 Drawing Sheets

(56) References Cited

OTHER PUBLICATIONS

Hoover et al.; "A novel method for RNA extraction from FFPE samples reveals significant differences in biomarker expression between orthotopic and subcutaneous pancreatic cancer patient-derived xenografts"; Oncotarget; vol. 8; 2017; p. 5885-5894.
Hedegaard et al.; "Next-Generation Sequencing of RNA and DNA Isolated from Paired Fresh-Frozen and Formalin-Fixed Paraffin-Embedded Samples of Human Cancer and Normal Tissue"; PLoS One; vol. 9; May 2014; 16 pages.
Karlsson et al.; "Amplification-free sequencing of cell-free DNA for prenatal non-invasive diagnosis of chromosomal aberrations"; Genomics; vol. 105; 2015; p. 150-158.
Myers et al.; "Reverse Transcription DNA Amplification by a Thermus thermophilus DNA Polymerase"; Biochemistry; vol. 30; Aug. 1991; p. 7661-7666.
Auer et al.; "Selective amplification of RNA utilizing the nucleotide analog dITP and Thermus thermophilus DNA polymerase"; Nucleic Acids Research; vol. 24; 1996; p. 5021-5025.
Trombetta et al.; "Preparation of Single-Cell RNA-Seq Libraries for Next Generation Sequencing"; Curr Protoc Mol Biol; vol. 107; 2014; 25 pages.
Murray et al.; "Sequence-specific cleavage of RNA by Type II restriction enzymes"; Nucleic Acids Research; vol. 38; 2010; 12 pages.
Fahy et al.; "Self-sustained Sequence Replication (3SR): An Isothermal Transcription based Amplification System Alternative to PCR"; PCR Methods and Applications; vol. 1; 1991; p. 25-33.
Gulliksen et al.; "Parallel nanoliter detection of cancer markers using polymer microchips"; Lab Chip; vol. 5; 2005; p. 416-420.
Schena et al.; "Parallel human genome analysis: Microarray-based expression monitoring of 1000 genes"; Proc. Natl. Acad. Sci. USA; vol. 93; Oct. 1996; p. 10614-10619.
Schena et al.; "Quantitative Monitoring of Gene Expression Patterns with a Complementary DNA Microarray"; Science; vol. 270; Oct. 1995; p. 467-470.
Nuwaysir et al.; "Gene Expression Analysis Using Oligonucleotide Arrays Produced by Maskless Photolithography"; Genome Research; vol. 12; 2002; p. 1749-1755.
Chee et al.; "Accessing Genetic Information with High-Density DNA Arrays"; Science; vol. 274; Oct. 1996; p. 610-614.
Albert et al.; "Light-directed 5' to 3' synthesis of complex oligonucleotide microarrays"; Nucleic Acids Research; vol. 31; 2003; 9 pages.
Gu et al.; "Protein tag-mediated conjugation of oligonucleotides to recombinant affinity binders for proximity ligation"; New Biotechnology; vol. 30; Jan. 2013; p. 144-152.
Piepenburg et al.; "DNA Detection Using Recombination Proteins"; PLoS Biology; vol. 4; Jul. 2006; p. 1115-1121.
Gansauge et al.; "Single-stranded DNA library preparation from highly degraded DNA using T4 DNA ligase"; Nucleic Acids Research; vol. 45; 2017; 10 pages.
Madabusi et al.; "RNA Extraction for Arrays"; Methods in Enzymology; vol. 411; 2006; 14 pages.
Stahl et al.; "Visualization and analysis of gene expression in tissue sections by spatial transcriptomics"; Science; vol. 353; Jul. 2016; p. 78-82.
Trombetta et al.; "Preparation of Single-Cell RNA-Seq Libraries for Next Generation Sequencing"; Curr Protoc Mol Biol; vol. 107; 2014; Supplemental 107; 17 pages.
Uyttendaele et al.; "Development of NASBAR®, a nucleic acid amplification system, for identification of Listeria monocytogenes and comparison to ELISA and a modified FDA method"; Int'l Journal of Food Microbiology; vol. 27; 1995; p. 77-89.
Fan et al.; "Combinatorial labeling of single cells for gene expression cytometry"; Science; vol. 347; Feb. 2015; 10 pages.
Picelli et al.; "Full-length RNA-seq from single cells using Smart-seq2"; Nature Protocols; vol. 9; 2014; p. 171-181.
Picelli et al.; "Smart-seq2 for sensitive full-length transcriptome profiling in single cells"; Nature Methods; vol. 10; Nov. 2013; p. 1096-1098.
International Patent Application No. PCT/US2017/056865; Int'l Search Report and the Written Opinion; dated Feb. 22, 2018; 18 pages.
International Patent Application No. PCT/US2017/056865; Int'l Preliminary Report on Patentability; dated May 2, 2019; 11 pages.
European Patent Application No. 17862593.5; Extended Search Report; dated May 26, 2020; 8 pages.

\* cited by examiner

Mount tissue to porous substrate

Deparrafinize & Hydrate
Incubate with reagents
(nucleases, antibody, etc.)

Contact tissue to barcode array surface

Image tissue, Digest tissue
Hybridize targets to array surface

HIGH RESOLUTION SPATIAL GENOMIC ANALYSIS OF TISSUES AND CELL AGGREGATES

CROSS-REFERENCE TO RELATED APPLICATIONS

The present application is the National Stage Application of International Patent Application No. PCT/US2017/056865 filed Oct. 17, 2017, which claims the benefit of and priority to U.S. patent application No. 62/409,265, "High Resolution Spatial Genomic Analysis of Tissues and Cell Aggregates" (filed Oct. 17, 2016), the entirety of which application is incorporated herein by reference in its entirety for any and all purposes.

RELATED APPLICATION

The present application claims the benefit of and priority to U.S. patent application No. 62/409,265, "High Resolution Spatial Genomic Analysis of Tissues and Cell Aggregates" (filed Oct. 17, 2016), the entirety of which application is incorporated herein by reference in its entirety for any and all purposes.

BACKGROUND

Over the past two decades, massively multiplexed analysis of mRNA (transcriptome) and DNA (genome) has advanced significantly through the development of a variety of sequencing approaches. These technologies, such as sequencing by synthesis (SBS) or next generation sequencing (NGS), allow the detection for example of the entire RNA transcriptome and the genome from a variety of sample types.

However, the overwhelming majority of methods requires a set of laborious steps to separate the nucleic acids from a complex tissue architecture, such as a tissue section or a blood sample. While they provide the ability to detect thousands of genes, these methods therefore result in the loss of spatial context, i.e. the specific location of the expressed or modified gene in a specific cell. In order to make better use of these tissue samples, and thereby limit the analysis of regions which are captured by chance, improved methods to provide high resolution analysis of spatial genomic, transcriptomic and proteomic are required.

There is a need for robust, easy to use systems that can achieve a complex combination of functional requirements (e.g., high resolution, positional specificity, complex sample handling, automation, high sensitivity, and massively multiplexed gene detection capability).

SUMMARY

In meeting the long-felt needs described above and to enable the ability to define cell specific lineage and delineate context specific genetic patterns in a massively multiplexed spatial specific manner, disclosed here are devices and methods related to transfer of genetic material from a tissue or cell sample to a surface that allows these specific analytes to be associated with the cells which these arose from within a complex sample, such as a slice of formalin-fixed paraffin embedded (FFPE) tissue sample.

Key advantages of the disclosed technology include, e.g., the ability to provide highly flexible, selectable regions of high resolution analysis of the expressed genes or proteins as well as the detection of genetic modifications that have occurred in a cell or a group of cells.

In the disclosed methods, genes present a specific cell within a tissue section are first transferred to a surface, which may be accomplished by a variety of methods. This surface may include a spatially specific arrangement of oligonucleotides, or barcodes, so to allow recapitulation of the sequences with the original tissue organization. By allowing imaging of the original tissue section combined with the ability to transfer these genes through hybridization from a specific cell to a specific annotated location in proximity to the cell of interest, the presently disclosed technology provides the ability to detect all genes expressed in a specific cell in a specific location in a tissue section at high resolution. Genetic signatures that are transferred can then be processed, tagged, amplified, and otherwise processed so to allow all genes or gene modifications in a specific location to be identified using methods such as NGS, for example. Because these genes are identified using a specific sequence in a specific position on the transfer array surface, the location of a specific transcript can be mapped back to the original location on the array and subsequently to the location or position in the tissue section.

In overcoming the problems associated with effecting spatial specific gene identification with a high throughput, low volume, fluidic sample imaging and molecular based NGS sample preparation platform, the disclosed technology is capable of performing sample preparation for the massively paralleled multiplexed detection and identification of a specific set of transcripts in a specific cell in a precise location of a tissue or multiple cell sample. The present technology provides, e.g., systems including a variety of integrated components, including reagent delivery and lysing apparatus, fluid manipulation componentry comprising a series of pumps and valves, thermal control regions, electrical current control, and plurality of barcoded oligonucleotides for resolving the location specificity of specific transcript. The present invention provides the ability to essentially detect all expressed genes, gene modifications, and proteins in an aggregation of cells by a variety of methods using an integrated sample preparation and discrete barcode array device.

In one aspect, the present disclosure provides systems, comprising: a plurality of base polynucleotides disposed on an amplification substrate; an optionally porous cellular support substrate, the optionally porous cellular support substrate and the amplification substrate defining a chamber therebetween; an inlet, the inlet optionally comprising an aperture formed in the cover, the inlet optionally placing the optionally porous cellular support substrate into fluid communication with the environment exterior to the optionally porous cellular support substrate.

Also provided are methods, the methods comprising: liberating nucleic acids from a cellular sample affixed to an optionally porous cellular support substrate, the cellular sample being capable of fluid communication with an amplification substrate bearing a plurality of amplification primers; translocating the liberated nucleic acids in a direction essentially perpendicular from the optionally porous cellular support substrate under such conditions that the liberated nucleic acids hybridize to the plurality of amplification primers, the liberated nucleic acids optionally being communicated in the direction of the plurality of amplification primers through the pores of a porous material; and amplifying the nucleic acids so as to give rise to amplification products.

Further disclosed are methods, comprising: liberating nucleic acids from a cellular sample affixed to an optionally porous cellular support substrate, the cellular sample overlying a plurality of amplification primers; translocating the nucleic acids in a direction perpendicular from the optionally porous cellular support substrate under such conditions that the nucleic acids hybridize to at least some of the plurality of amplification primers, the liberated nucleic acids optionally being communicated in the direction of the plurality of amplification primers through the pores of a porous material; amplifying the nucleic acids so as to give rise to amplification products; and associating at least some of the amplification products with locations within the cellular sample.

Also provided are sample preparation systems for high resolution spatial genetic analysis, comprising: (a) a sample preparation module material capable of attaching a cellular sample to an optionally porous cellular support substrate that allows imaging of the tissue or cell aggregate or tissue section sample on one side, and provides the ability to deliver reagents to the sample; (b) a sample preparation module material that allows chemical fixation of a cellular sample to occur on the surface of the optionally porous cellular support substrate; (c) a sample preparation module that is chemically inert to non-polar solvents; (d) a sample preparation module capable of treating the cellular sample treated with reagents to label proteins with nucleic acid sequenced tagged antibodies, aptamers or any other ligand to bind to a specific protein with a cell in the sample; (e) a device capable of imaging of the cellular sample in close proximity to an array of oligonucleotides to coordinate the tissue sample location with each oligonucleotide element on the array; (f) a sample preparation module that seals the integrated device so as to prevent lateral fluid flow during migration of the target nucleic acids and so as to effect fluid flow over a bar-coded array of oligonucleotides; (g) a module by which samples are digested with proteolytic enzymes, including but not limited to proteinase or protease to release one or more sample templates; (h) a module that effects migration of charged nucleic acid templates to the array surface in an x-y plane such that (i) the process of (f) is effected such that sample templates are migrated under the control of electrophoresis and/or (ii) the process of (f) is effected so samples migrate to the array surface under the control of z-directional flow generated by pressure of elec-trokinetic flow; (i) at least 20,000 oligonucleotide probes on the array, (i) optionally in the array, the areal density of probes being equal to or greater than the density of the areal density of cells that reside on the optionally porous cellular support substrate, (ii) at least some of the oligonucleotide probes comprising a set of first array sequences that in combination with a second set of barcode sequences form a hybrid pair with the 3' end exposed so as to serve as a hybridization and primer element on the array, (iii) at least some of the set of first array sequences being synthesized in reverse order with the 3' end exposed that serves as a hybridization and primer element on the array, (iv) a set of array sequences that contain a primer sequence on the 3' terminus, which may include an oligo dT sequence, a specific primer sequence, or a random sequence, (v) a plurality of oligonucleotide probes that include a sequence that effects quantification of the copy number of sample template molecules, (vi) a plurality of probe elements that comprise a plurality of barcoded oligonucleotides associated with the location, presence, or both of a genetic element specific to a cell, a cell region, regions or the entire array, (vii) a barcode array that comprises a number of distinct barcode sequences that allow amplification or enrichment of a selected area on the array, (j) the system being configured such that one or more reactions can be conducted on the array surface, the one or more reactions comprising the use of one or more of a RNA or DNA dependent DNA polymerase, a ligase, exonuclease, or endonuclease so as to provide the ability to create a barcoded first strand cDNA, (k) the system being configured so as to allow first strand reaction products to be released from the surface using a restriction endonuclease or temperature to release the first strand cDNA, (l) the system being configured so as to allow a process that provides a sample that can be transformed into a sequencing library with known barcode sequences which can be split into individual reactions to provide a sample that is sequenced at high read depth using next generation sequencing.

Additionally disclosed are fluidic devices to perform high resolution spatial genomic analysis, comprising: a sample preparation module, a series of fluidic channels and an array of oligonucleotides disposed on a conductive surface within the device so as to allow for one or more of sample addition, fixation, paraffin removal, incubation, sample imaging, active control target of sample nucleic acid templates, and multistep molecular biology reactions to effect sample preparation, hybridization, reverse transcription and first strand cDNA synthesis of sample templates with the device.

Also provided are methods for spatially resolving protein and/or nucleic acids from biological samples, comprising the steps of: mounting a sample to a porous surface; hydrating the sample; placing the sample into fluid communication with a second surface that having a barcode disposed thereon and the second surface being electrically conductive; obtaining positional information regarding the sample relative to the barcode array; digesting the sample so as to release nucleic acid targets; translocating the targets to the barcode array of the second surface so as to effect hybridization; effecting sequencing of the hybridized targets; correlating results of the sequencing so as to positionally resolve the location within the sample from which one or more targets originated.

Thus, provided herein are, inter alia, integrated methods of biologic sample preparation and analysis using systems that conduct the steps required to prepare a sample for high resolution spatial genomic analysis. The device and associated method enable the preparation of a tissue section or cell aggregate sample to be affixed to the sample preparation module, then imaged and processed to allow release of the template nucleic acids. Said template nucleic acids are then transferred through an active process which captures the sample nucleic acids in a spatially specific manner that is coordinated with the original location of the templates in the tissue sample. Having hybridized the sample templates to a high-density oligonucleotide array which contains a plurality of spatially defined barcoded primers, the templates can then be copied through either reverse transcription and/or the polymerase chain reaction to enable amplification of the template copies.

Upon completion of the multistep molecular biology reactions, the resultant barcoded cDNA molecules can then be released from the oligonucleotide array to further prepare the sample for sequencing analysis. Upon completion of the sequencing analysis, the detected oligonucleotide sequences arising from either RNA, DNA or proteins in the tissue are then recombined with the original image to provide a spatial genomic map of the expressed genes, gene modifications or proteins in each cell, or a specific grouping of cells in the tissue section or cell aggregate sample. The systems and assay processes described herein can be performed in a completely automated fashion. The disclosed systems are robust, simple to use, and address the goals of the medical diagnostic community to provide improved therapeutic decision making for patient care and therapy.

BRIEF DESCRIPTION OF THE DRAWINGS

The foregoing summary, as well as the following detailed description, is further understood when read in conjunction with the appended drawings. For the purpose of illustrating the invention, there is shown in the drawings exemplary embodiments of the invention; however, the invention is not limited to the specific methods, compositions, and devices disclosed. In the drawings.

As shown in the FIG., a given region of a sample substrate (bottom image) may, upon magnification, provide a set of samples, which set may include subsets that include BC2 and BC1 oligonucleotide barcodes, a subset of samples that includes BC2 and BC3 barcode oligonucleotides, a subset that includes BC2 and BC2 (twice) oligonucleotide barcodes, and a subset that includes BC2 and BC4 oligonucleotide barcodes.

Figure 4:
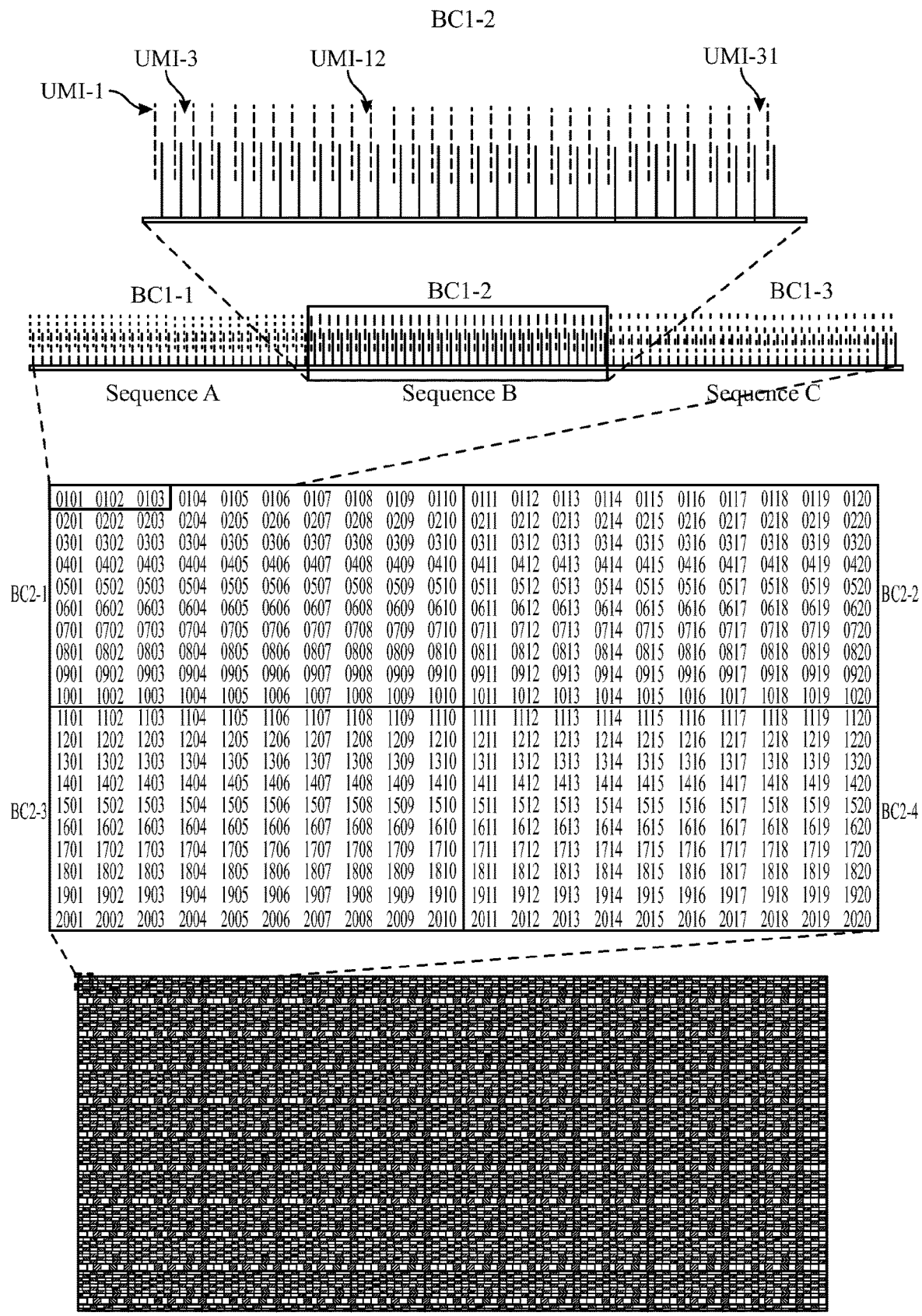
FIG. 4 is an embodiment of the barcoding structure of the oligonucleotide array. The array structure using two distinct barcode sequences in each oligonucleotide allows identification of each individual barcode in addition to a shared barcode that creates a regional sequence for a group of individual barcoded oligonucleotides.
Figure 5A:
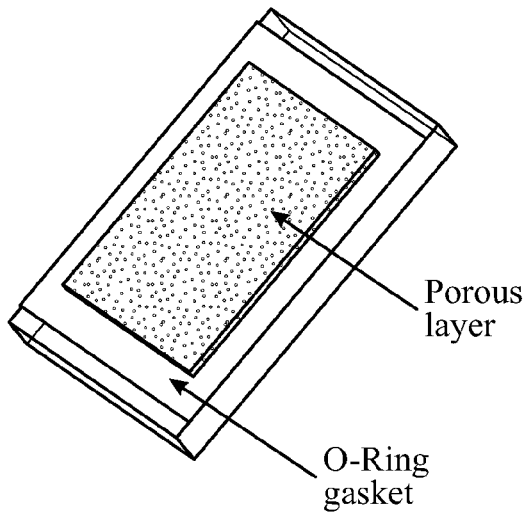
Figure 5B:
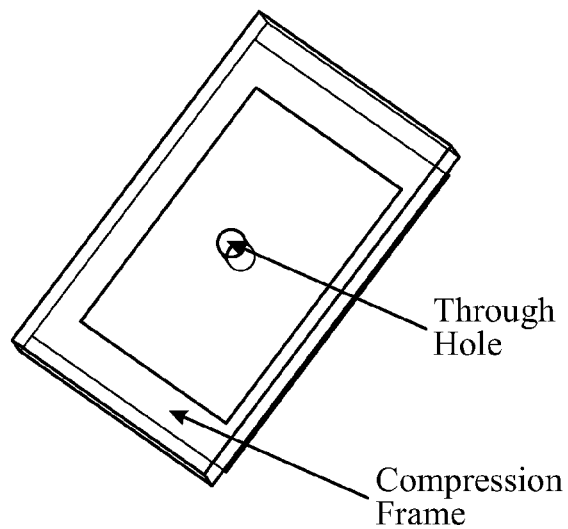
Figure 5C:
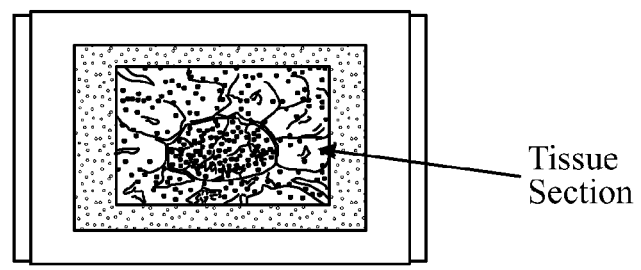
Figure 5D:
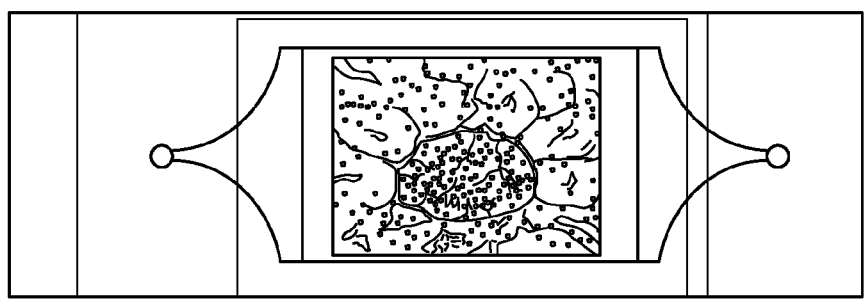

Examination of a sub-region of the BC2-1 set (second image from top of FIG. 4) provides that the sub-region may include Sequence A, Sequence B, and Sequence C of interest as shown. As shown, each of these three sequences may include different BC barcode oligonucleotide identifiers. Further examination (top image in FIG. 4) provides that different members of the Sequence B sub-region may in turn have different UMIs associated with them.

FIG. 5 is a tissue mounting device allowing attachment of a tissue section or cell aggregate on the surface of a porous material which allows reagent delivery and contact of sample with the barcode array.

Figure 6:
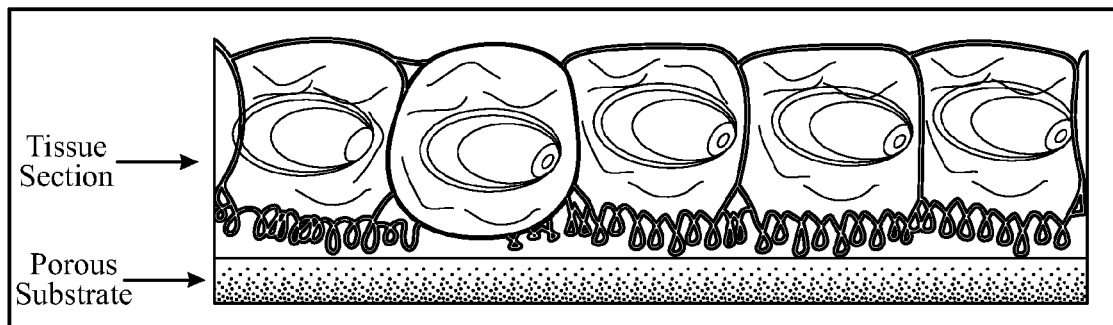
Figure 6:
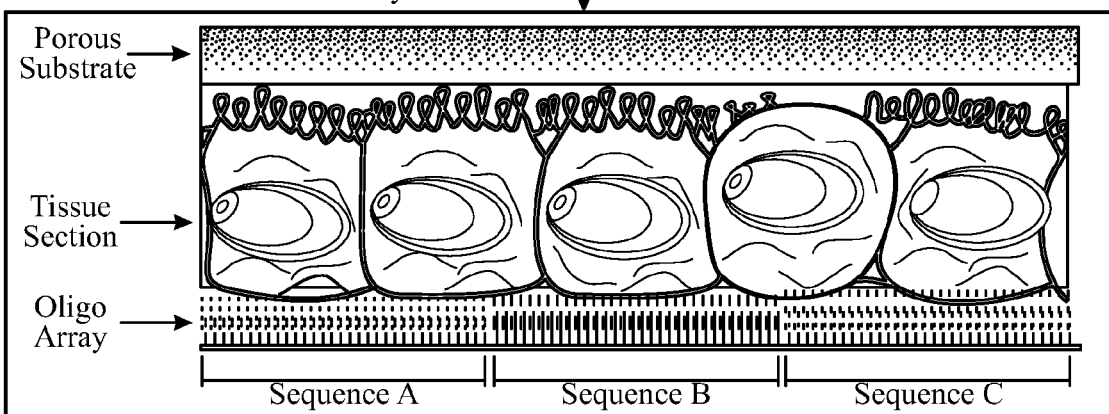
Figure 6:
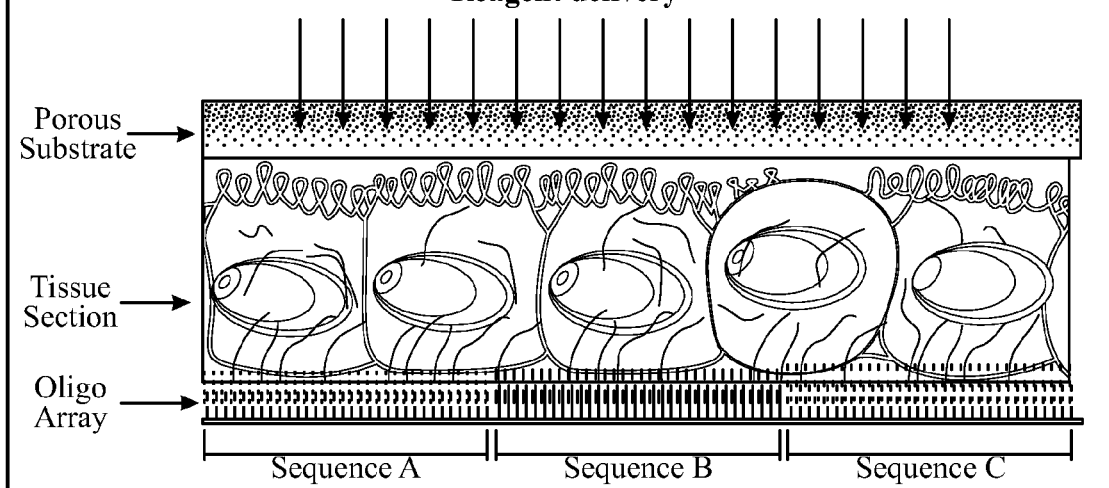

FIG. 6 demonstrates a process for assembling a tissue section on the mounting device, the mating of the mounted tissue to the array, the digestion of the proteinaceous or non-target materials and hybridization of the released target nucleic acids on the barcode array surface. As shown in the FIG., one may image the tissue to determine precisely which region of the tissue overlies which region of the oligonucleotide array.

Figure 7A:
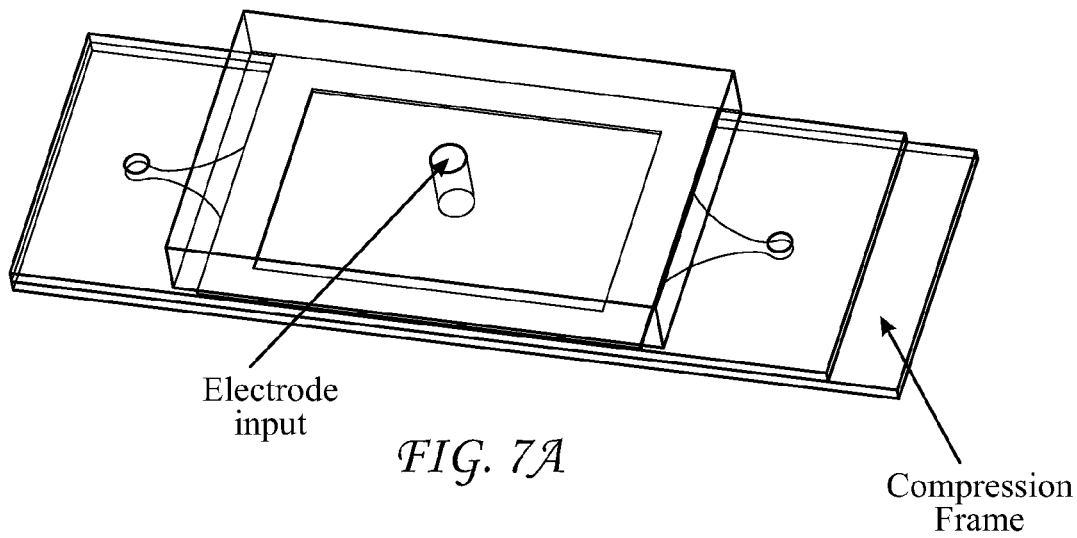
Figure 7B:
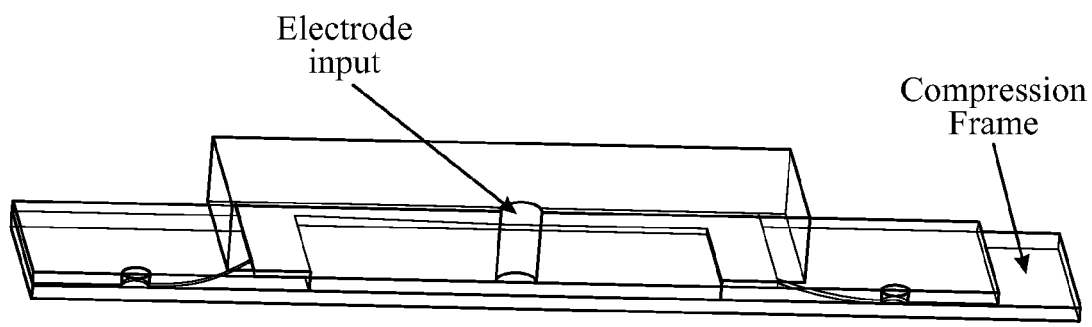

FIG. 7 is a perspective embodiment of the device which demonstrates how the sample templates are actively migrated to the array surface. The device contains two electrical conductive input/outputs where the sample can be contacted by two electrodes, one where the fluid may be contacted by an electrode, and second a conductive surface which contains the oligonucleotide array. The figure demonstrates how the electrical current is directed from the sample region to the array surface to enable active control of the hybridization of the sample templated with the array of oligonucleotide primer elements.

Figure 8:
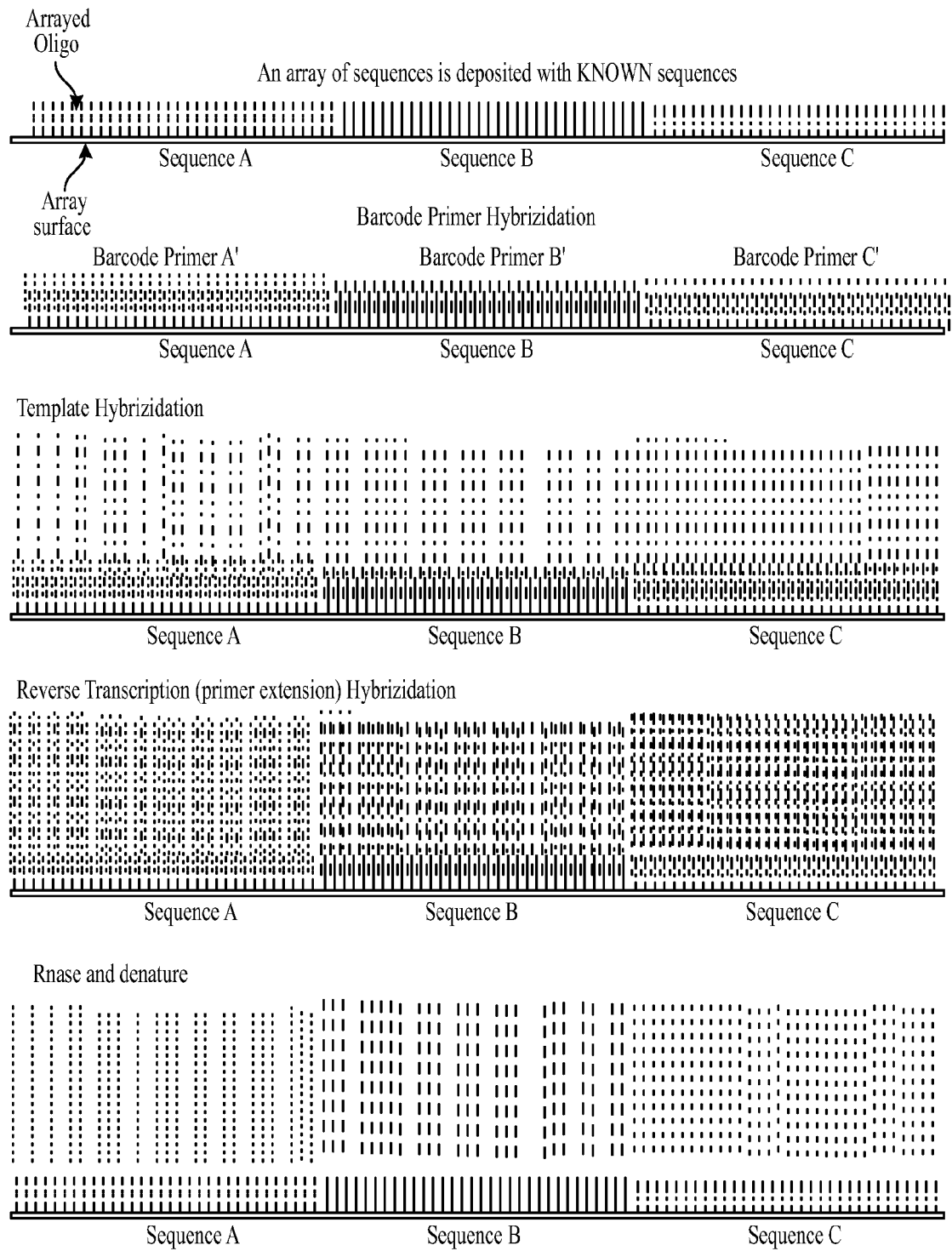

FIG. 8 demonstrates the process in which the high resolution and tiled barcode array is assembled; the target analytes hybridize the extension of a barcoded primer and release of the resultant first strand DNA molecule.

Figure 9:
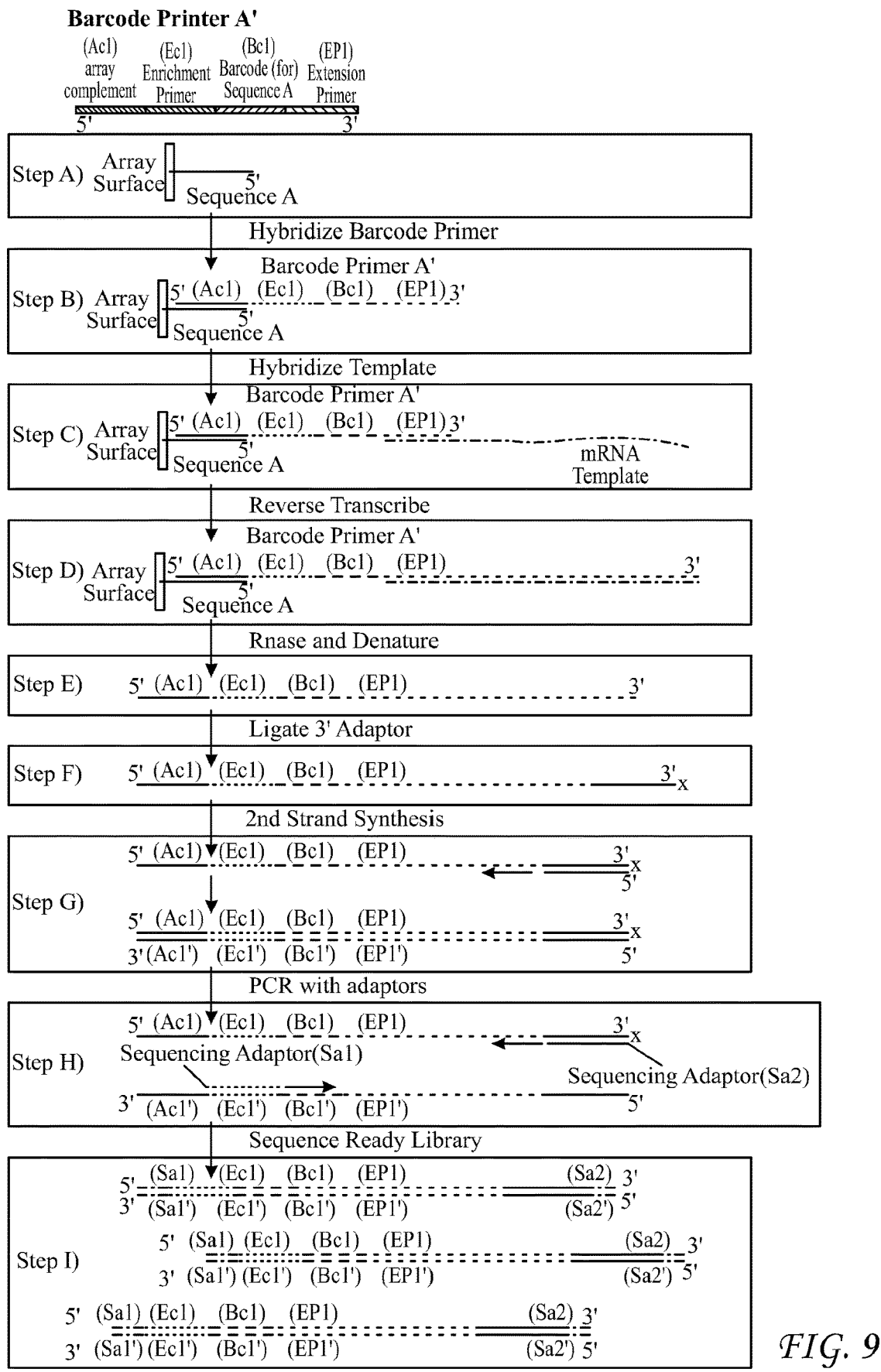

FIG. 9 is an example of a nucleic acid hybridization and processing that results in sequencing-ready library of molecules for NGS analysis. This library may include information regarding, e.g., the spatial location of the cell from which certain nucleic acids were liberated. The library includes all nucleic acid sequences that were transferred and copied during the preparation of the sample. Nucleic acid sequences may consist of RNA (either mRNA, rRNA, or tRNA), DNA, or oligonucleotides that are linked to antibody. Antibody linked oligonucleotides, for example, are used to define the presence of specific protein in the tissue sample. Using multiple antibodies (e.g., up to several thousand) can allow delineation of the proteomic signature of each of the cells in the sample.

During the transfer of the nucleic acid sequences, due to the arrangement of the oligonucleotide primers that are located on the array, the spatial location of each (RNA) transcript, DNA sequence or antibody that was present in the cell can be mapped back to the original image of the cell sample. In this way the genomic and proteomic signature of each cell in the sample can be coordinated with the morphology of the cell. This information is particularly helpful in understanding the resulting phenotype of a cell which results from its underlying genomic and proteomic structure. In the case of heterogenous cancer samples, as one illustrative example, the disclosed approach can assist in understanding why certain cells respond to therapy, while others are resistant. In another example, the system can allow the understanding of why certain immune cells within a tumor are inactive (not killing the tumor), while others are active killing cells, which is the current basis of much of the immun-onocolgy studies.

DETAILED DESCRIPTION OF ILLUSTRATIVE EMBODIMENTS

The present invention can be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, can also be provided in combination in a single embodiment. Conversely, various features of the invention that are, for brevity, described in the context of a single embodiment, can also be provided separately or in any sub combination. Further, reference to values stated in ranges includes each and every value within that range. Any documents cited herein are incorporated herein by reference in their entireties for any and all purposes.

It is also to be understood that the terminology used herein is for the purpose of describing particular aspects only and is not intended to be limiting. As used in the specification and in the claims, the term "comprising" may include the embodiments "consisting of" and "consisting essentially of" Unless defined otherwise, all technical and scientific terms used herein have the same meaning as commonly understood by one of ordinary skill in the art to which this invention belongs. In this specification and in the claims which follow, reference will be made to a number of terms which shall be defined herein.

As used in the specification and the appended claims, the singular forms "a," "an" and "the" include plural referents unless the context clearly dictates otherwise. Thus, for example, reference to "a virgin polycarbonate" includes mixtures of two or more virgin polycarbonates. Furthermore, for example, reference to a filler includes mixtures of fillers.

Ranges can be expressed herein as from one particular value, and/or to another particular value. When such a range is expressed, another aspect includes from the one particular value and/or to the other particular value. For example, a range of "1 to 10" includes all intermediate values, e.g., 3, 5.56, and 7.3. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated +/−10% a variation unless otherwise indicated or inferred. For example, "about 10" encompasses the range from 9 to 11, including 10. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

The terms "first," "second," "first part," "second part," and the like, where used herein, do not denote any order, quantity, or importance, and are used to distinguish one element from another, unless specifically stated otherwise.

As used herein, the terms "optional" or "optionally" means that the subsequently described event or circumstance can or cannot occur, and that the description includes instances where said event or circumstance occurs and instances where it does not. For example, the phrase "optionally substituted alkyl" means that the alkyl group can or cannot be substituted and that the description includes both substituted and unsubstituted alkyl groups.

As used herein, the term "effective amount" refers to an amount that is sufficient to achieve the desired modification of a physical property of the composition or material. For example, an "effective amount" of a recycled polycarbonate blend refers to an amount that is sufficient to achieve the desired improvement in the property modulated by the formulation component, e.g. splaying, under applicable test conditions and without adversely affecting other specified properties. The specific level in terms of wt % in a composition required as an effective amount will depend upon a variety of factors including the amount and type of recycled polycarbonate blend, amount and type of virgin polycarbonate polymer compositions, amount and type of impact modifier compositions, including virgin and recycled impact modifiers, and end use of the article made using the composition.

Disclosed are the components useful in preparing the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary.

For example, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific aspect or combination of aspects of the methods of the invention.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent ("wt %") of a component, unless specifically stated to the contrary, is based on the total weight of the formulation or composition in which the component is included. For example if a particular element or component in a composition or article is said to have 8% by weight, it is understood that this percentage is relative to a total compositional percentage of 100% by weight.

Compounds are described using standard nomenclature. For example, any position not substituted by any indicated group is understood to have its valence filled by a bond as indicated, or a hydrogen atom. A dash ("—") that is not between two letters or symbols is used to indicate a point of attachment for a substituent. For example, —CHO is attached through carbon of the carbonyl group. Unless defined otherwise, technical and scientific terms used herein have the same meaning as is commonly understood by one of skill in the art to which this invention belongs.

Fluidic componentry and methods are used to perform ultra-high density analysis of biologics associated in a spatially specific manner in a tissue or cell aggregate sample. Improved systems and methods that integrate an ultra-high density, specific and sensitive assay scheme into a robust front-end sample preparation is presently needed. For example, imaging systems and sample preparation methods are needed that enable the operator to perform an analysis in a three-step process: (1) affix the sample; (2) prepare the sample and (3) process the sample in an automated fashion. In addition, the information reported should permit high consequence decisions to be made, demanding that the system's assay be specific and give correct prognostic information. These technical requirements are also desired in an assay and the system that are exceptionally robust. Existing approaches to performing multiplexed detection, however, are deficient and warrant improvement [1-12].

Accordingly, there is a need to develop systems and assay methods that are capable of having the following characteristics:

Ability to identify genes in cells in a discrete location within a cell.

Ability to image tissue in an orientation of an ultra-high density tiled array of barcoded oligonucleotides.

Ability to prepare sample for contact with an array of spatially defined oligonucleotides Prepare sample to release sample templates to allow for hybridization Ability to combine, through active means, the genetic material in a sample with an array of barcoded oligonucleotides in a spatially specific manner.

Ability to prepare samples for massively multiplexed detection of the genetic material within each cell in the sample.

Assembly of a series of image maps that combine the location of a cell in a tissue or cell aggregate within a spatially defined array or oligonucleotides that are representative of all gene transcripts, gene modifications, or oligonucleotide sequenced tagged proteins.

Ability to Identify Genes in Cells in a Discrete Location within a Cell

The disclosed technology enables hybridization, through active methods, of a sample template with an array of oligonucleotides to provide a complimentary base pair of a template and a primer. In order to maintain the spatial resolution of a genetic sequence within a tissue, methods are disclosed to combine a sample template molecule with a primer through complimentary base pairing of DNA or RNA to maintain the location of this genetic material in a sample. Similar to creating a copy of an image, the nucleic acids from the sample are combined with an oligonucleotide, a primer, so as to create an image of all genes and gene modifications in a specific location, a cell, within a tissue sample.

To allow detection of this genetic material, the disclosed technology provides the ability to barcode each gene or genetic element in a given cell in a spatially specific manner. This technology further allows the amplification of each of the barcoded genetic sequences to allow preparation of the sample for sequencing analysis. In this way, each gene of each cell can be identified and mapped back to the original location within the sample, using the spatially defined barcode oligonucleotide. In connection with the disclosed technology, provided herein is an apparatus that allows contact of the sample with an array of spatially defined oligonucleotides to bring the sample into contact with this array. Further, the apparatus allows the preparation of the sample to enable the hybridization through complimentary base pairing of a nucleotide sequence in the sample with a barcode oligonucleotide present on the array surface. Suitable examples of a sample include a FFPE tissue sample, a cell aggregate, or cell smear or a frozen fixed section of tissue. Suitable examples of the array of barcodes include a high-density microarray (e.g., having more than 3000 spots), or an array of nucleotide sequences deposited upon a generally planar surface.

The apparatus allows imaging of the sample in a location-specific manner, which may be performed in combination with the oligonucleotide array to create an image map that provides coordination of the location of the sample with the array or oligonucleotide sequences deposited upon the microarray. Using this system, each and every cell in a specific location of the tissue or the entire section of tissue can be analyzed. Using the disclosed methods allows the selection of critical region for analysis and allows rejection of areas that are either not populated by cells or of areas that are not of interest.

Image Tissue to Provide Spatial Map of Genetic Signatures

A critical feature in the ability to understand the biological mechanisms underlying observed functionality, such as the pathology of cancer, is to clearly identify the genetic attributes of both the pathologic and non-pathologic cells within a tissue. Pathologists routinely use their training in histopathology to determine the state of a group of cells in a normal or abnormally functioning tissue sample. They simply understand what appears normal and what does not. However, while techniques to observe a single or a few specific molecular signatures exist, using, for example In Situ Hybridization (ISH) in the context of the individual cells, performing global analysis of the genomic structure within these areas or cells is not currently possible.

Because diseases such as cancer are complex and arise from many changes in the DNA structure and multitude of alternatively expressed genes, the ability to truly understand the basis of disease depends on putting the variety of these modifications in context with the actual cells residing in the tissue sample or cell aggregate sample. The disclosed technology allows the association of the histological attributes with the genomic structure by creating an image map of the tissue in combination with transfer of the genetic material to a surface that can be spatially resolved and used to prepare the transferred macromolecules for analysis. In this way, the entire genetic code can be further analyzed and mapped back to the cells or regions where these macromolecules resided in the tissue sample or cell aggregate sample.

This is accomplished by mounting the tissue to a transparent media, such as glass or fused silica, to image this section or cell aggregate and provide the ability to either transfer the macromolecules from the tissue to a surface or alternatively transfer the spatially resolved molecular identifiers (i.e. barcoded oligonucleotides) into the tissue. Several methods are disclosed herein whereby tissue is mounted to a porous substrate so as to allow both imaging of the specimen and combination of the macromolecules from the tissue with an array of spatially resolved elements, such a DNA primer.

Mount and Prepare a Tissue Section for Imaging and Nucleic Acid Transfer

Suitable samples that can be analyzed by the methods disclosed herein include, but are not limited to, cell aggregates, cell smears, tissue samples, and liquid samples such as blood. In many cases these tissue samples are preserved using fixatives including but not limited to para-formaldehyde, glutaraldehyde, and formalin, which create chemical cross links in the proteinaceous tissue. These tissues are further processed to preserve the structure of the tissue in paraffin-embedded blocks or cubes, which allow the pathologist to create thin sections of the material for histological examination.

The tissues undergoing this process are typically referred to as Formalin-Fixed Paraffin-Embedded (FFPE) samples. However, while the samples are convenient for histopathologic methods, they are less well-suited for direct global genomic analysis. In order to liberate nucleic acids from these samples, a typical workflow includes removal of the paraffin using a series of non-polar solvents in a tube to allow precipitation of the sample between solvent washes. This allows paraffin removal while retaining the target sample in the vessel or tube.

This process may be followed by digestion of the sample with a protein digestive enzyme such as Protease or Proteinase K. This digestion removes the cross-linked proteins from the sample by cleaving the peptide bonds that provide the sample its structure. This process results in a sample that contains a soluble fraction in solution which contains cleaved peptides and liberated nucleic acids, including, depending on the process, intact DNA and RNA. This solution is then further purified to remove the soluble protein fraction to yield a highly enriched sample of nucleic acid.

Often, this process includes digestion of DNA and/or RNA depending on the experimental procedures. A drawback of this procedure is the loss of the relationship of the location of nucleic acids in the actual cells and the position of these cells within the tissue sample. In fact, the majority of procedures to isolate nucleic acids utilize a similar process to purify the nucleic acids for downstream analytical techniques, including real time PCR, and sequencing applications. The processes in almost all cases result in the loss of the relationship of the nucleic acids with the cells in which this DNA originated. Although the processes do enable detection of abundant gene transcripts (mRNA) or gene modifications (DNA) from the homogenous sample, these techniques also suffer a loss of sensitivity in that they rely on detecting a differentially expressed gene in a large mix of normal gene signatures. This is why the plethora of single cell technologies have been developed to provide increased resolution at the cellular level. Here again, however, the single cell techniques rely on creating a suspension of live cells to allow compartmentalization of the cell necessary for analysis of the single cell. These techniques include microfluidic partitioning of the single cells or compartmentalization of the cell in a droplet to allow amplification and detection of the intracellular macromolecules, such as RNA [4-7, 12, 13].

In addition, the overwhelming majority of these techniques rely on the use of live cells, as the buoyancy of the cells is critical for compatibility with these partitioning workflows. Other approaches provide analysis of tissue in a random manner of regions which may or not be important.

As a result of these aforementioned limitations disclosed here, techniques to allow the analysis of each or a specific selection of cells in a tissue and the coordination of the genetic and proteomic signatures with each cell in a massively multiplexed manner are still lacking. To enable this process, several methods are disclosed herein to allow a high-resolution mapping of the tissue to be collected prior to the analysis of the genetic and proteomic material that resides in each cell. In order to create this image, the tissue is mounted upon a substrate that allows viewing using standard microscopy techniques that allow imaging of the tissue in relationship to various fiducial markers that provide the specific position of the tissue in relationship to a series of oligonucleotides that contain specific sequences which are orientated with a specific position within an ultra-high dense array of oligonucleotide barcodes.

A first step in preparing the tissue or cell sample for this imaging step is the mounting of the sample upon a substrate that allows the sample to be affixed to the substrate. This substrate can take many forms. The material selection of this substrate will depend on the type of sample and the steps required to prepare contacting the sample to the oligonucleotide barcode array. In some cases, the substrate will be porous to allow both tissue adherence to the surface of the substrate combined with the ability to perform downstream steps that include delivering reagents through this substrate to the tissue sample or cell aggregate sample.

In other cases, the substrate may be non-porous where the oligonucleotide array can be configured to dissolve into the tissue sample. In any event, the critical step is affixing the sample to a semi-rigid material to allow imaging of sample in context of the barcode array.

Material selection of the substrate used to affix the sample will also depend on the solvents required to prepare the sample for contact with the barcode array. For example, an FFPE sample that requires paraffin material removal will require a substrate which is inert to the effects of the solvent. Examples of such materials include borosilicate glass, fused silica, PFTE, or other material that is inert to the solvents typically used to remove paraffin, such as toluene, or chloroethylenes, or any other highly non-polar solvents used for paraffin dissolution. By contrast, samples such as smears, cell aggregates, or single cell suspensions that do not require paraffin embedding and therefore do not require solvent based removal of the paraffin, can be mounted on substrate materials including thermoplastic polymers and plastics, in the steps required to prepare the samples for contact and transfer of the nucleic acids from the sample to the barcode array.

The complete workflow, while having some variation based on the procedure required, suitably supports two steps:

First, construction of a spatially specific image map, based on the arrangement or location of the target cells in the tissue sample or cell aggregate sample and an array of barcode oligonucleotides, and Second, the ability to combine the sample templates, through complimentary base pairing or hybridization with an arranged set of and ultra-high density set of oligonucleotides which allows recapitulation of the arrangement of the cells and the barcode position. In this way, all expressed genes in a specific location, co-located to the position of a cell of interest, can be reconstructed to identify all variations arising or present in a single cell, or even the sub cellular location of the genetic elements within the cell of interest.

Several methods are typically employed to affix a cell or tissue sample to a substrate to accomplish imaging of the sample. As an example, when a tissue sample is sectioned from an FFPE sample it is typically shaved from the surface of a paraffin block, e.g., in a thickness of from about 4 to about 20 microns. This section is then most often placed in a water bath to allow softening of the paraffin and allow the tissue to return to its nominal arrangement (i.e., planar) or structure. This results as the tissue section has less density than the water in the bath so it floats on the surface, which is flat. After several minutes in the bath, tissue sample is usually transferred to a planar substrate, such as a borosilicate glass slide where it is allowed to dry. The sample that contains both a paraffin layer and the fixed tissue is then baked for a period of time at temperatures typically below 100 deg. C. and above 30 deg. C., most commonly around 65-70 deg. C. This process typically facilitates the adherence of the tissue sample to the substrate.

Often, specialized slides with alternative surface treatment of chemical modification are used. These modifications may include poly-lysine deposition and the like to promote the adherence to the substrate. Alternative methods of affixing a cell sample (such as a smear or a cell aggregate) to a substrate may include the application of an alcohol such as methanol, isopropyl alcohol or ethanol to assist in the adherence of the tissue or cell sample to the substrate. This step may be conducted when the sample is still wet to prevent shrinking of the cells that are desired to be imaged for histopathology. These methods can be used in the current embodiment disclosed herein. As an example, a tissue sample can be affixed to a porous substrate, provided the material allows adherence of the tissue sample to the substrate. In other cases, a non-porous material can be used to affix the sample. In this case the contact of the sample with the barcode array can occur between two non-porous structures or a combination of non-porous with porous substrates. The selection of this combination is dependent on the steps required to prepare the tissue to contact with the device to allow complimentary base pairing of the genetic material in the sample to the array of barcodes that are present on the array surface, as shown in FIG. 5.

The image map of the tissue is suitably created with appropriate resolution to determine the sub cellular structure of each cell in the tissue. Such image resolution can be achieved using a variety of microscope objectives in combination with a light microscope which has at least one or several wavelengths of light that can be detected. Typical resolution can be achieved using objectives which can detect and resolve features of about 20 microns or less. Optimally, images are acquired at a higher resolution and subsequently stitched or combined to create a tiled map of the tissue section. Higher-power objectives, such as 4, 10, 20, 40, 60, 100× may be further employed provided they have appropriate working distance from the sample. Higher magnification allows smaller features to be resolved, such as the nucleus of a given cell or in some cases the location of other cellular organelles, such as the rough endoplasmic reticulum, smooth endoplasmic reticulum, Golgi, or mitochondria or other organelles present in the cell. The working distance of a particular objective is a consideration, as the image map is created with reference to the barcode oligonucleotide array, e.g., FIG. 6. In order to create the spatially specific map, the sample must be in contact or close proximity to the barcode array prior to collection of the image. In this way, specific fiducial markers that are arranged in the barcode array provide the location of a cell in reference or provide a direct relationship location of the barcode in reference to a cell in the tissue sample or cell aggregate sample, e.g., FIG. 5.

Prepare Sample to Release Sample Templates to Allow for Hybridization

To enable detection of genetic material in a sample, analytes of interest may be liberated from the tissue sample or cell aggregate sample to allow hybridization through complimentary base pairing with the barcoded oligonucleotides placed upon the array surface. In contrast to other work, the tissue is prepared to limit the diffusion of the analytes to off target locations.

In a preferred embodiment, the mounted tissue that has been processed to remove any interfering substances, e.g., paraffin, is placed upon the array surface as an intact tissue sample. Once assembled into the device (e.g., FIG. 5), the sample must be processed to allow liberation of the intact genetic material that is maintained in the ultra-structure of the cell by protein crosslinks formed during the fixation of the sample. After imaging within the device containing the array of barcoded oligonucleotides, the sample can then be digested to allow the liberation of the genetic material within the sample (e.g., FIG. 5).

A number of methods may be employed to remove these chemical crosslinks within the tissue sample. One method commonly used to digest a proteinaceous sample is the use of serine proteolytic enzymes. The use of these enzymes as opposed to simply permeabilizing the tissue sample of cells allows, in the disclosed embodiment, the ability to perform analysis of RNA transcripts, DNA fragments, as well as proteins using sequenced tagged protein binding reagents.

These methods can be used to release the target molecules from the sample to allow for hybridization of the sample templates with the array of barcoded oligonucleotides. Typically, these solution based reactions include at least one proteolytic enzyme such as proteinase K or Protease, a detergent, such as Triton X-100™, sodium dodecylsulfate, or sarcosine, and optionally contains a chaotropic reagent such as guanidine thiocyanate or hydrochloride and a buffer to maintain neutral pH such as sodium phosphate [14, 15]. The reactants in solution act in concert to cleave the peptide bonds between the amino acids of the proteins and disassociate the cleaved proteins. As these proteins become soluble, target nucleic acids are liberated and available for hybridization. Further additives may be added to the reaction mix to either further inhibit the activity of nucleases and to promote stable base pairing, such as aurintricarboxylic acid, tetraethyl ammonium chloride (TEAC) or Tetramethylammonium chloride (TMAC), respectively. Using this combination of water soluble reagents, a sample is treated so as to initiate the digestion of the proteinaceous sample. This process may be comparatively rapid in the case of a cell aggregate or cell smear, which contains only a few cells in a lose configuration, while more organized and highly cross linked tissue samples may take longer (e.g., hours) to digest.

Complete dissolution is not required, while release of the template molecules is required. These liberated template molecules are then available for hybridization with an oligonucleotide which enables the co-location of the template:oligonucleotide pair and the location of the cell of origin in the tissue. The oligonucleotide may include several sections, an enrichment primer sequence, a 1st barcode sequence which identifies where the oligonucleotide was deposited within the array and a 2nd barcode sequence and, a random sequence to assess the uniformity of amplification [16, 17], and finally a template primer sequence that facilitates hybridization to the template sequence which can be used with the combination of an RNA or DNA polymerase to make a complimentary copy though extension of the primer when hybridized to the template sequence. Optionally, an array complementary sequence is included in the oligonucleotide, which in some embodiments may be used to locate oligonucleotide in a specific position on the array, e.g., FIG. 2. As described, several methods may be used to solubilize the sample to facilitate release of the template genetic material and hybridization with the array of oligonucleotide primers, but all methods simply facilitate the ability to combine the sample templates with the array of oligonucleotides to provide a high resolution spatial map of the genetic elements in the tissue in a spatially specific manner.

Ability to Combine, through Active Means, the Genetic Material in a Sample with an Array of Barcoded Olignucleotides in a Spatially Specific Manner One method to allow spatial genomic analysis is to contact the sample which resides on a surface that is placed in direct contact with second surface that contains the oligonucleotide array. It may be preferable to maintain a static, no flow environment so as to limit diffusion of either the template or the oligonucleotide primer, thereby maintaining the locational specificity of the complimentary base paired template and oligonucleotide primer hybrid.

By keeping the sample in close proximity or in direct contact with the high-density oligonucleotide array, the distance from the sample to the high-density oligonucleotide array is minimized. It is also preferable to control the migration; while the diffusion distance and time required to create the complimentary base paired template and oligonucleotide primer hybrid is then minimized, active steps may be used to provide high resolution mapping of the genomic sequences in the tissue specimen. Once this hybrid pair is combined (and provided the pair is not separated during subsequent steps), the location of the template arising from the cell of interest can be identified by the barcode sequence in the primer in combination with the original location of the barcode oligonucleotide on the array.

In one disclosed arrangement, the sample is placed upon a porous substrate. With the sample affixed to the porous substrate, reagents that promote the release of the sample template can be communicated through the membrane. The diffusion through the porous layer of the proteolytic enzymes or reagents that render the sample permeable allow the release of the sample template from the surface bound porous material, which is in contact with the array of oligonucleotide primer complex on the array surface (e.g., FIG. 5). In this arrangement, one part of the oligonucleotide complex is covalently attached to the array, while a second oligonucleotide is complimentary base-paired to the first covalently surface bound oligonucleotide, and then the second oligonucleotide, upon contacting the tissue, allows for complimentary base pairing with the template from the sample (e.g., FIG. 8). As the sample begins to dissolve or becomes permeable, the templates are liberated from the sample and diffuse out of the surface bound tissue. Due to Brownian motion of the released sample template, these nucleic acid sequences can migrate in the opposite or adjacent directions from oligonucleotides upon the array surface. This random motion may result in a loss of the resolution of the spatial nature of the genomic expression.

In order to control the migration of the template, an active force is applied that minimizes off target complimentary base pairing events. In this arrangement, the sample template is conducted from the tissue location to array surface under an electrophoretic applied force, though other forces besides electrophoretic forces are suitable.

To enable this force to be applied, the sample is surrounded by appropriate aqueous solvent, so that charged molecules such as nucleic acids are actively moved from the sample to the array surface. This may be accomplished by creating an electrical potential between two poles that surround the sample and the oligonucleotide array. As one example, on electrical pole may be located above the sample and one pole is located beneath the array surface (FIG. 7). By applying electrical current, charged molecules will migrate from the sample to the target oligonucleotides complex that is covalently linked to array surface. This uniform electrical field promotes efficient movement, overcoming Brownian motion, to conduct the sample template from the affixed tissue sample to the array surface, which increases the resolution of the spatially derived genomic information located in the sample. In combination with a high-density oligonucleotide array, the active control of the migration of the sample template to the array provides enhanced spatial resolution of genomic elements within the tissue sample.

Other methods can be used to provide the force required to conduct the template from the sample to the oligonucleotide array. In one preferred embodiment, both the first substrate which the sample is affixed to and second substrate which the oligonucleotide array is attached to are porous. Upon conducting the reagents through the first substrate, the released templates are conducted by fluid motion to the second porous substrate where the surface-bound oligonucleotides are located.

Although there are several methods to conduct the template from the sample to the oligonucleotide array, one feature of the disclosed technology that provides high resolution spatial genomic analysis is controlling this migration and providing a high resolution array of oligonucleotides to maintain locational specificity of the sample template within the tissue sample.

Upon forming complimentary base pairs between the sample template and target and surface bound oligonucleotide hybrid, a second step may be employed to remove unwanted interfering substances by washing the array surface. After washing is complete, a second reaction is employed to create a complimentary copy of the template, using a RNA- or DNA-dependent DNA polymerase such as a reverse transcriptase or DNA polymerase. This first-strand cDNA synthesis reaction allows the incorporation of one or several location-specific barcodes and also of the enrichment primer into the complimentary copy of the template sequence (FIG. 8). Depending on the sequence used for the complimentary base pairing of the template molecule and the oligonucleotide primer, one or more templates can be copied. In the simplest example, a sequence that is specific for a given gene can be used. In this way, all cells within the tissue may be analyzed for the presence of one gene. Alternatively, a series of sequences can be used, using a common barcode, in each position of the array.

In this way, several genes can be analyzed in tandem in each cell within the tissue sample that is in contact with the plurality of oligonucleotides present on the array surface. In another embodiment, the primer structure of the oligonucleotide may be common to all expressed genes, for example eukaryotic mRNA that contains a polyA tail. In this case, the primer element in the oligonucleotide barcode will contain an oligo dT sequence that will hybridize to all sequences that contain a polyA tail or sequence. When this hybrid pair is formed between the template molecule and the oligonucleotide primer, in combination with a RNA dependent DNA polymerase (i.e. reverse transcriptase), then all mRNA molecules arising from a cell of interest can be processed to create a first strand cDNA molecule which contains a sequence of a gene of interest in combination with the elements present in the oligonucleotide primer, such as the barcode sequence and the enrichment primer element.

Methods for Creation of the Complimentary Copy of the Sample Template Molecules

One of skill in the art will appreciate that ultrahigh spatial analysis may require several general steps, which steps may include, e.g., 1) sample pretreatment, such the removal of paraffin, 2) sample imaging, where the sample is imaged while in close proximity to the high density oligoarray, 3) release and hybridization of the sample templates to the high density array, using for example permeabilization reagents such as detergents, proteolytic enzymes nucleases, 4) removal of debris after the permeabilization and hybridization step, 5) creation of the first strand copy of the template primer complex, 6) harvest of the resulting first strand copy and 7) attachment of the 3' amplification sequence to the complimentary first strand product.

It should be understood that variations of each of these steps are possible. Such steps are discussed here generally in order of the aforementioned order, but may also be described separately in greater detail and may not reflect this exact order. This is a result of differences in molecular biology that may require variation on this general protocol. The aforementioned process of preparing the sample for forming the complimentary base paired hybrid with the primer is a critical step in performing spatial genomic analysis. However, in order to analyze the sample hybrid using sequencing analysis, steps are required to prepare a library of molecules for NGS analysis from the hybridized sample templates. Most next generation sequencing technologies require the incorporation of known oligonucleotide sequences into the individual molecules that are analyzed. The samples are typically then amplified and purified to prepare them for use in a sequencing flow cell. In the current embodiment, these steps take the following general steps.

Upon creation of the hybrid pair of the primer and the template, as mentioned the first step is the creation of the complimentary copy of the template. This may be accomplished by combining this sample template:primer pair with a reaction mix that contains a number of substrates including nucleotides, a buffer, such as Tris-EDTA, a polymerase and a salt typically magnesium chloride. Additives are often used to stabilize various base pairing combinations, such as betaine, TEAC, TMAC, or trehalose to augment the activity of the enzyme and often contain a blocking reagent such as bovine serum albumin (BSA) to limit the amount of non-specific absorption of the enzyme in the reaction vessel. If target molecule of the sample template is an RNA species, most often an RNA dependent DNA polymerase is employed to perform reverse transcription reaction, one where a RNA molecule is copied, resulting in a first strand cDNA molecule which is an exact complimentary match of the RNA template (FIG. 9). Several types of enzymes can be employed to perform this reverse transcription, including but not limited to Reverse Transcriptase M-MuLV, Moloney Murine Leukemia Virus, Reverse Transcriptase, AMV from avian myeloblastosis virus, Tth DNA Polymerase which is recombinant enzyme with both intrinsic transcriptase and thermostable DNA polymerase activity [18, 19]. Additionally, the reaction mix may contain an inhibitor of the proteolytic enzymes.

To enable amplification of the first strand cDNA molecule, typically an adaptor sequence is added to the 3' end of the complimentary first strand cDNA. There are several methods to achieve the inclusion of the adaptor sequence, notably a template switch process, where an additional oligonucleotide is used to serve as a template to the primer molecule that is being extended. This adaptor sequence can then be used as a primer, optimally the same primer sequence as the enrichment primer sequence to amplify the cDNA sample. Several other techniques includes the ligation of adaptor to either the RNA:DNA duplex, or creation of a second strand cDNA with a random primer that contains adaptor, or the ligation of a random primed first and second strand DNA:DNA duplex after shearing and size selection. These techniques are aimed toward providing enrichment primer sequences at the 3' and 5' flanking ends of a single strand of cDNA, enabling the amplification of the double stranded template for further preparation and sequencing library creation.

Having encoded the adaptor sequence into both flanking ends of the cDNA, the template can then be amplified using either a common enrichment primer or a combination of primers. The reaction is then thermal cycled to perform a polymerase chain reaction using a thermal stable DNA dependent DNA polymerase. Selection of enzymes is important for this stage of the reaction as the templates have a variable length in some cases up to 10 kbases. Enzymes that can be used to perform this reaction include but are not limited to SeqAMP, BST, and klenTaq enzymes.

Isothermal amplification techniques may be further employed to amplify the resulting first strand cDNA. An example of such reaction is the recombinase amplification reaction [31]. In this arrangement, the can either be combined with the reverse transcriptase step, or conducted after the RT and 5' handle attachment is complete as individual steps. Isothermal methods offer the further advantage that they can be conducted on the array surface as they use temperatures in the range of 37-42 deg. C.

Template Switch: One method of creating the enrichment primer on both the 3' and 5' end of the molecule is to use the template switching property of viral RNA dependent DNA polymerases [20]. This method uses an oligonucleotide that serves as the template towards the 3' end of the transcript cDNA complimentary copy being created during the reverse transcription reaction. In this reaction scheme, at the 3' terminus of the gene, the polymerase switches the template, using and RNA dependent DNA dependent DNA polymerase and a template switch oligonucleotide and creates a complimentary copy of this oligonucleotide at the end of the molecule. The output of this reaction is a cDNA that has amplification primer at both 3' and 5' encoded into the ends of the molecule, enabling PCR amplification of the synthesized cDNA.

Ligation: Another method of encoding the reverse primer into the 3' end of the complimentary cDNA copy is the use of ligation in the RNA:DNA hybrid [21]. In one embodiment, in order to create a 3' adaptor region on the RNA:DNA hybrid molecule formed during the RT reaction, a restriction enzyme is used to cleave the end of the molecule and insert a double stranded strand of oligonucleotides at this terminus. At the conclusion of this reaction, the RNA is degraded and the cDNA containing both 3' and 5' primer sequences is amplified through PCR.

Random priming: An alternative method for creating the second strand of cDNA is the use of a random primer. In this reaction scheme, the first strand cDNA is contacted by a primer that has a random sequence that allows a DNA dependent DNA polymerase to extend this primer in the opposite direction of first strand cDNA creating a second strand of cDNA. If the random primer contains a second primer sequence at the 5' end of the primer, then this second strand reaction encodes an amplification primer at the 5' end of the second strand molecule. In this way, the second strand molecule contains both and 3' and 5' primer sequence that can be used for PCR amplification.

T7 amplification primer: As an alternative to encoding a second primer sequence in the first strand molecule of the cDNA, this molecule can be amplified using 3SR [22], NASBA [23, 24], TMA amplification. In this arrangement, a sequence allows a specific enzyme to create multiple copies of the first strand cDNA with having a complimentary second strand. Having created many copies of RNA using T7 RNA polymerase, this molecule is converted to cDNA. These amplified sequences are then used to create a sequencing library using a variety of methods.

Single stranded ligation methods for adapter addition: As an alternative to providing a 3' adaptor on the complimentary strand through the use extension methods (template switch) or linear amplification (T7 amplification), several methods have been developed to ligate an adaptor using either circligase (reference) or T4 DNA ligase (reference), using a random splinter ligation oligonucleotide [32]. In this embodiment, after RT has been conducted and the first strand oligonucleotide has been harvested from the consumable device, the released RNA/DNA hybrid is first digested with RNaseH, then subjected to the ligation protocol to attach a 3' handle on the complimentary strand that contains the necessary sequence to amplify the various DNA regions corresponding the regions of the tissue section that was mated to the array.

Various Modes of Creating a First Strand Molecule on the High Density Array.

There are various modes of creating the hybrid that allows the first strand molecule to be created. Once formed, this hybrid pair can then be further collected from the device for further processing to allow NGS analysis of all genetic elements from the sample. In this way, all genetic elements analyzed have a barcode sequence that references where the template molecule arose from in a spatially specific manner in the tissue sample. One element that may be present in these approaches is ensuring close contact of primer and sample template and active migration of the template to the surface bound primer.

In one embodiment, the primer on the high-density surface is covalently bound, but is synthesized in the reverse direction from the 5' at the surface of the array to the 3' terminus to provide a covalently bound primer structure with the 3' end exposed to enable direct priming and the formation of a complimentary copy of the template from the sample. Methods for the arraying such molecules with the 3' end exposed are well known. These methods typically utilize a robotically deposited spot [25, 26].

These methods, however, are limited to the array density that can be deposited. Using these methods, a oligonucleotide array is deposited using a non-contact or contact printer which creates an array of DNA spots with a 60-300 diameter feature that are separated center to center by approximately 1-2× distance of the spot size. The use of these relatively large features, compared to the cells in the tissue (around 10-30 microns) may result in several cells being present in each DNA spot, and leaves relatively large gaps between each area that is interrogated.

Using a high-density oligonucleotide array fabricated on a conductive layer approach solves this problem by first creating small features that are roughly half the size of an average cell. Due to the increased density of the barcoded array, the control of the migration becomes critical to maintain the high resolution spatial genomic approaches. In this embodiment, the surface bound primers may contain a specific sequence or sequences in the 5' end to allow a restriction enzyme, endonuclease or exonuclease to cleave this extended primer from the array surface after creating a complimentary copy of the sample template nucleic acid molecule. Alternatively, the primers may be linked to the surface using a reversible bond, such as a disulfide or any other covalent or ionic bond that can be undone or otherwise cleaved. The arrays may be fabricated leaving a 3' end exposed upon the conductive layer so as to create a high density array of primers which can form a primer:sample template complimentary primer pair. As in the aforementioned example, the templates are directed to the surface of the array under an active force, such as electrophoresis [27, 28, 29].

In this embodiment, the samples can either be cleaved from the surface to be prepared into a library for downstream sequencing analysis or alternatively used to perform in situ sequencing by synthesis analysis. Such sequencing approaches can be integrated in the device for sample preparation to perform integrated end to end analysis of the tissue section to provide spatially and location specific arrangements of genetic elements within the tissue of origin.

In summary, the assay has several significant advantages over other molecular diagnostic assays. These include the following:

All Expressed Genes, Gene Modifications or Sequence Tagged Proteins within a Cell can be Detected.

Using the disclosed technology, all genes in a particular site can be interrogated and also referenced back to the cell of origin. In addition, using a similar schema, all proteins can be analyzed in the sample. Methods for the interrogation of proteins in tissues are well established using several molecular approaches to bind a macromolecule such as an antibody or aptamer to the protein within the sample. In one embodiment, the macromolecular reagent used to bind this sample bound protein is modified to include a nucleic acid sequence tag [30]. Using these sequence tagged reagents, the tissue can then be used in a similar IHC protocol to bind the reagents to the tissue. Once bound to the tissue, having removed or washed off the unbound materials, using the same aforementioned protocol, the sequence tags of these reagents can be transferred to the barcode oligonucleotide array for complimentary copying, amplification, and sequencing. In this process, the use of enzymes to digest the proteins becomes important, as to properly form a hybrid pair the sequence tag should be released from the protein recognition reagent.

The expressed genes, gene modifications, or sequence tagged proteins, can be annotated to a specific location of a cell in a sample. Using the described protocols, the gene and proteins detected from the array can be recapitulated with the original image of the tissue section or cell aggregate sample. Combining the high resolution genomic analysis of features that are smaller than the cells of interest provides the ability to interrogate most, if not all cells, within the entire tissue section. Alternatively, the use of tiled barcodes can be used to interrogate only specific areas of choice.

In one embodiment, two barcode sequences are used on the first strand cDNA primer. In this way one serves as the regional barcode sequence, while the second cell barcode can be used to code for specific sub region or a specific cell within tissue. The barcodes can be used in combination during a series of enrichment PCR reactions as the regional primer will enrich for a group of cells, whereas the cell barcode can be used to amplify the genes coordinated with a specific cell. Alternatively, the barcodes can used be in combination, during a first enrichment PCR reactions, as the regional primer for a group of cells, whereas the cell barcode can be used to detect, through sequencing analysis, the genes coordinated with a specific cell. This is particularly useful as the number of surface bound barcoded primers using the high-density array will produce more sequencing reads that is capable of being effectively read out during the sequencing of the cellular material.

Because the array may contain roughly 500,000 to six million attached barcode oligonucleotide primers, the ability to sequence all of these cDNAs will provide low sequencing depth. As current sequencing flow cells contain enough sequencing depth to provide approximately 400,000,000 reads per flow cell, this only provides the ability to analyze approximately 1000-2000 cells, with about 200,000 to 400,000 thousand reads per cell. In this way, each sequencing reaction can be PCR enriched separately and run in a distinct sequencing flow cell, providing the ability to analyze all cells in a particular tissue sample. This process allows high depth sequencing a few cells, or alternatively low depth sequencing of a high number of cells. The depth of sequencing is of course dependent on the experimental question. However, the ability to discriminate cells based on phenotype from gene expression (mRNA signatures) can be accomplished using a relatively low number of reads/cell or sequencing depth. In addition to enabling the detection of phenotypic differences by gene expression as a proxy for the expression of a given protein, the disclosed method can also confirm phenotypic differences by detecting directly the expression of protein.

The system allows detection of these gene modifications in samples that have been stored or preserved for long periods of time. One of the hallmark events in the development of cancers is the modification of a parent gene in the genome. These modifications can take a variety of forms including: a single base mutation, a re-arrangement, a deletion, or amplification of a given gene. A modification of the workflow can be employed to detect these alterations in the genome. For example, a specific barcoded primer can be designed to form a complimentary hybrid pair with a specific sequence in the genome.

To employ this technique, the DNA must be released from the tissue in a size range that is convenient to create an encoded copy that can form a complimentary base pair with the surface bound oligonucleotide primer. Several methods of creating the required size of DNA have been developed including shearing the DNA, sonication the DNA, and fragmenting the DNA by using an enzyme. One method of creating a certain size range of template DNA is the use of a restriction enzyme or endonuclease. The use of these enzymes creates double strand breaks in the DNA and depending on the amount of enzyme and the duration of the incubation can create DNA fragments in the size range from approximately 200 bases to 2000 bases. This fragmented DNA can then be hybridized to the array surface, where it is then copied using a DNA dependent DNA polymerase. Using this process modification allows the analysis of even fragmented DNA from tissues that have been preserved for extended periods of time. This is a highly useful feature as retrospective studies are now possible to create a map of cells in a tissue sample that are causative and to combine this with classical histopathology.

Illustrative Embodiments

A device according to the present disclosure (e.g., FIG. 1) may be an integrated system to allow imaging of an aggregation of cells allowing transfer of the nucleic acids in the sample to a high density oligonucleotide array, and to actively move the templates from the sample to the array. In addition, the device contains a through hole at the top of the device to supply reagents and access to an electrode to form an electrical potential between the through hole, and the array surface which contains a conductive layer. The device further contains both input and outlet channels to allow the introduction of reagents for additional reactions and washing steps to facilitate sample preparation of the transferred templates that are hybridized on the array surface. The top component of the device is a compression frame that allows samples to be deposited and compressed on to the array surface.

An exploded drawing of the device (FIG. 2) shows a detailed description of the device construction. From the bottom up the device contains a base layer that contains a high-density array of barcoded oligonucleotides. The structure of the aforementioned oligonucleotides (FIG. 3) may have several sections as previously described. In this embodiment, the oligonucleotide attached to the array surface has 6 sections. The barcode array is formed or deposited using array based oligonucleotide synthesis in such a way the array is tiled (FIG. 4) to enable selection of the regions of interest for further analysis.

In this way, each oligonucleotide probe on the surface has two barcodes (FIG. 3), one that is specific to the individual probe (the cell barcode) on the surface and a second barcode that indicates a region or a selection or group of individual cell barcodes. The high-density oligonucleotide array may be housed in a chamber created by several layers that are assembled upon the substrate used for the barcode array. These layers typically will include a channel layer, that will be fabricated from an adhesive, and a fluidic interconnect that will be formed from an extruded or thermoplastic resin.

Several other components are combined to create the sample preparation compression frame (FIG. 5). The components (FIG. 2) may include a porous substrate such as porous glass, optionally an adhesive layer to secure this material to the compression frame, and gasket material to allow the channel to be sealed during sample dissolution. In this arrangement, the sample placed directly upon the porous substrate can be processed to remove, if necessary, the paraffin used to embed the sample. Having removed the paraffin, the sample upon the porous substrate is combined with the compression frame (FIG. 5C) and inserted into the device to place the sample in intimate contact with the barcode array (FIG. 5D).

Having the sample in close contact with the array, the sample can be further processed to release the template nucleic acids to allow complimentary base pairing with the barcode oligonucleotides on the high-density array surface (FIG. 6). With the sample affixed to the substrate (as shown, the substrate in FIG. 6 to which the cells are mounted is porous—but a porous substrate is not a requirement) and combined with the compression frame (FIG. 5), the sample can now be placed in direct contact (or fluid communication) with the array surface (FIG. 6) and come into close contact (or fluid communication) with the arrayed oligonucleotides. With these cells in close contact (or fluid communication), the sample can now be processed.

Reagents may be conducted through a porous substrate so as to come in contact with the sample, though this is not a requirement, as reagents may be introduced to the sample in other ways besides the "back side" of the sample if the sample is mounter on a porous substrate.

It should be understood that one may use a non-porous layer in the disclosed technology; cells may be attached to a non-porous layer and then be processed so as to liberate nucleic acids. In this arrangement, rather than conducting the reagents through the porous layer, they can be introduced through an alternative inlet, e.g., a channel in the same plane of the sample. This channel height can be controlled through the design of the device, to both minimize the distance between the sample and the array, while also providing an appropriate channel height to introduce reagents. As one example, a tissue sample may be positioned from about 1 to about 50 micrometers from the array, allowing reagents to be introduced in the space between the sample and the array. In this embodiment, one may control the flow of reagents so as to ensure diffusion and/or to ensure that fluid movement is minimized during the active nucleic acid transfer step.

Figure 1:
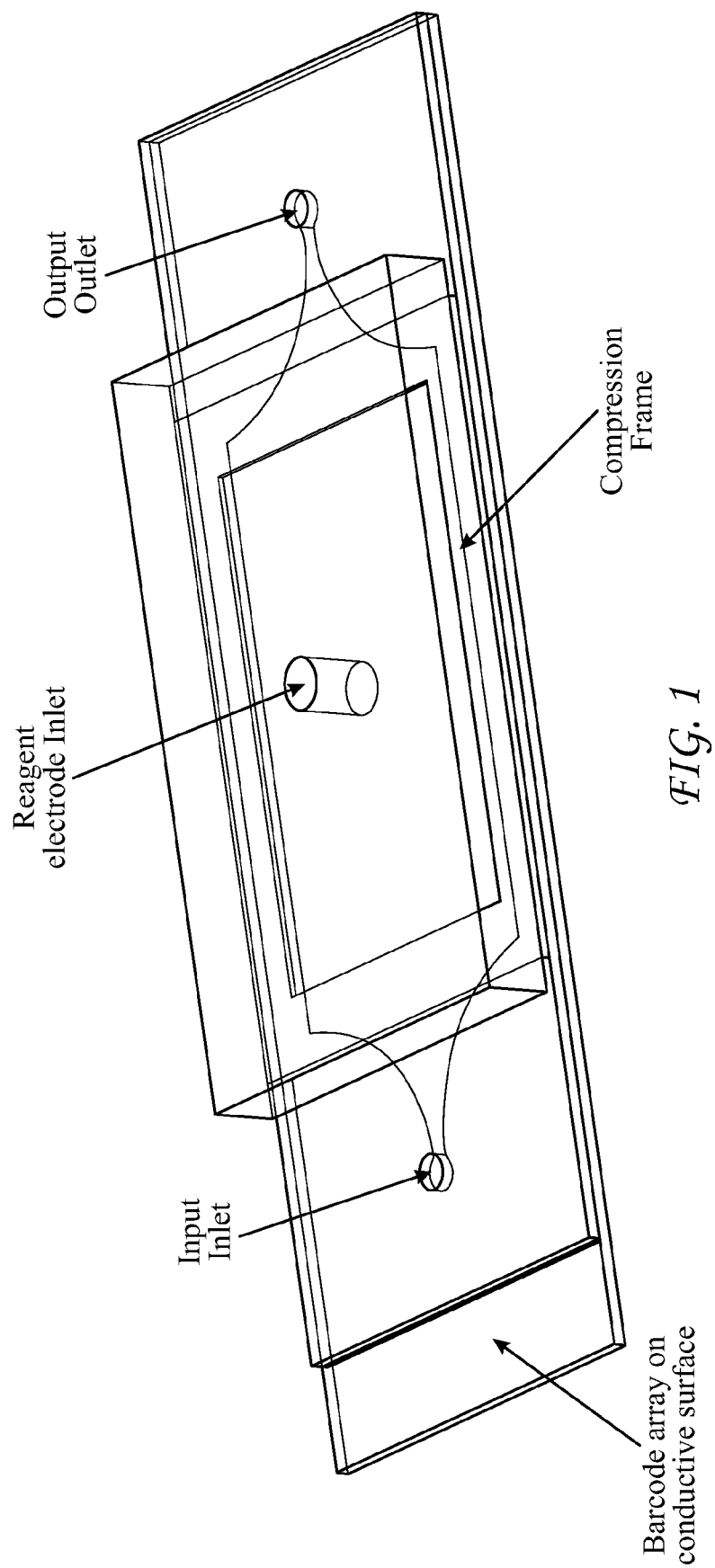
FIG. 1 is a top perspective of an embodiment of the sample preparation and analysis system of the present invention.
Figure 2:
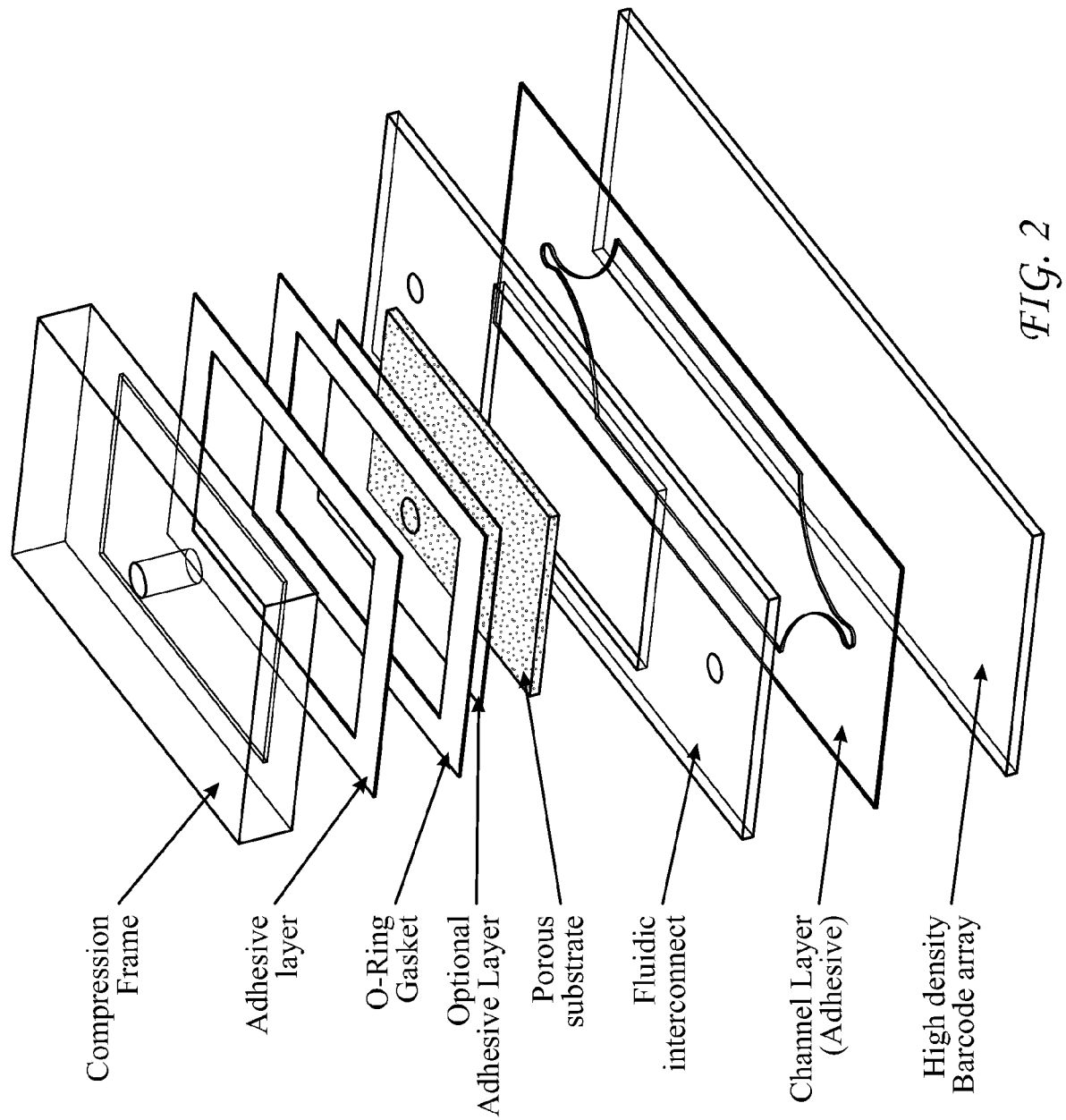
FIG. 2 is a top perspective of an embodiment of the sample preparation and analysis system of the present invention that shows the layout of the internal components.

This may be illustrated by reference to FIG. 1 and FIG. 2, with the modification that the compression frame does not include an aperture formed therethrough. In such an embodiment, a cellular sample may be attached to a cellular support substrate located where the "porous substrate" is shown in FIG. 2; the cellular support substrate need not be porous. After the device is assembled with the cellular sample attached to the substrate, one or more reagents may be introduced by way of the "input inlet" shown in FIG. 1, and excess material may be removed by way of the "output outlet" shown in FIG. 1. In this way, reagents need not necessarily be introduced by way of the "back" of the substrate on which cells are disposed; instead, reagents (e.g., lysing reagents) may be introduced into the space between the cell sample and the array facing the cells. The reagents need not necessarily be introduced into a side of a device; reagents may be introduced by way of an inlet formed essentially anywhere in a device, e.g., by way of an inlet formed in a substrate the supports the array, by way of an inlet formed in the side of a chamber that defines a volume between a cell sample and an array, or an inlet formed elsewhere.

The reagents in this step digest the tissue, effectively releasing the nucleic acids from the tissue. These nucleic acids are then conducted from the sample to the array surface using an active force and begin to hybridize with the array. It should be understood that a capillary plate or other porous medium may be disposed between the sample and the array so as to maintain linear motion of material between the sample and the array and minimize "drift" or sideways motion of material that is being communicated from the sample toward the array.

Figure 7C:
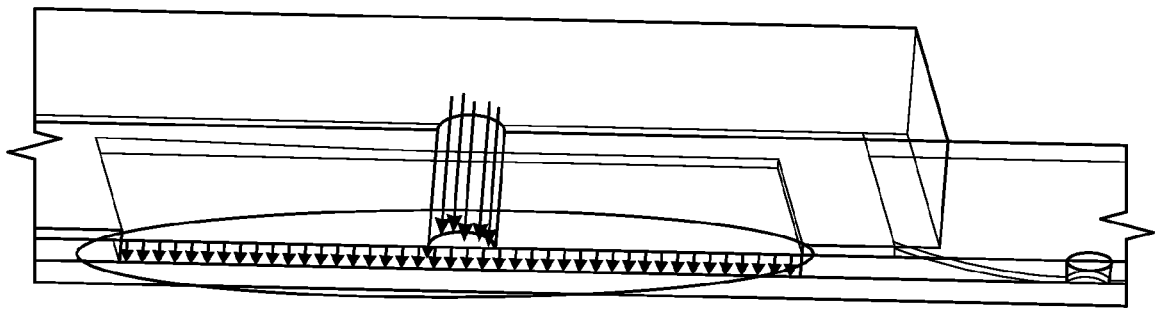

One active force that is convenient for methods of translocating charged molecules from one location to another is the use of electrical potential or electrophoresis. This may be done by creating a uniform conductive layer on the substrate used to deposit the oligonucleotide array (FIG. 7). Having the sample in contact with the array and in the presence of the aqueous reagents used to process the sample provides the ability to create a potential through the assembled device. In this case a potential will conduct the sample template toward the oligonucleotide array (FIG. 7C).

Having actively transported the sample templates to the array surface, the complimentary base pairing can occur (FIG. 8). The array surface may include a near-contiguous layer of oligonucleotide sequences that differ in several portions of the sequence. There are several arrangements of the primers on the array, however a critical feature is having the 3' end of the oligonucleotide exposed to allow the primer to extend when having formed a complimentary base pair.

On the array are two sets of oligonucleotides, one oligonucleotide set that is fabricated on the array, with the 5' end exposed, and a second barcoded set of primers, that forms a complimentary pair with the surface tethered oligonucleotides. In combination this base paired double stranded molecule that has one strand that has its 3' end exposed, serves as a spatially located set of primers that can produce a complimentary copy of the each template in the sample provided it can hybridize. Once the hybrid has formed, a range of reactions can be conducted. In the case of mRNA, a reverse transcription reaction is often used to create cDNA that can be further amplified. After the complimentary copy of the RNA, or the cDNA, is made, these templates can simply be denatured from the surface of the array.

An RNase reaction to remove the template RNA may be conducted as well, however this is completely dependent on the target analyte selected for analysis. As previously mentioned, the system can prepare RNA, DNA, and proteins for analysis. DNA for example would not require a reverse transcription step, only the use of DNA dependent DNA polymerase.

Breaking the reaction steps into segments is useful to understand the flexibility and further potential of the disclosed technology (FIG. 9). As seen in step A, an oligonucleotide having a known sequence, is applied, affixed, or synthesized in a specific and known location on a surface (array surface). In step B of FIG. 9, a primer that has several components, is hybridized to the surface-bound oligonucleotide, with the Bc1 sequence referencing or otherwise being correlated to the Ac1 sequence, so as to be able to locate the origin of the primer after creating a complimentary copy of the sample template, amplification of this copy, and sequencing analysis.

A primer may contain several sequences, and may contain more or less depending on the requirements for selection of the regions and cells for downstream analysis. The primer will always contain a 3' end that allows the extension of the primer in the presence of a polymerase. In step C (FIG. 9), the template molecule hybridizes to the extension primer (EP1) sequence, which can be extended in either an RNA or DNA dependent DNA polymerization. Upon the reverse transcription of first strand synthesis of the template molecule, one or several steps can be employed to add an adapter on the 3' end of the cDNA molecule. As discussed, there are several methods to add this adaptor, including but not limited to ligation, template switching, and the use of random PCR primers. Having attached this adaptor, second strand synthesis can then occur, followed by amplification of the cDNA and or inclusion of further adaptors for sequencing based analysis. After amplification, depending on the size of the sample template fragments, further steps may be required to prepare a library for sequencing based analysis. In these steps, the BC1 and (optional BC2) sequences are suitably preserved in the amplicon that is eventually sequenced.

Upon completing the sample preparation and sequencing analysis, the data is converted back to a file that can be analyzed to associate the gene of interest and the location barcode with the cell or region of interest. The data can be handled in several different manners.

The device is controlled by an instrument that can additionally perform fluid and thermal control while conducting various reagents and buffers to the device to enable the steps required for high resolution spatial genomic mapping. The device instrument further allows imaging of the sample after placed into the device. Optical communication of photons emitted from the device therein can be accomplished using an optical coupling situated between the assay device and device. Suitable optical couplings include an optical waveguide, a lens or series of lenses, an optical fiber bundle, a transparent (e.g. glass or plastic) rod, a fiber plate, an aperture, a filter set, or any combination thereof. In certain preferred embodiments of the present invention, the optical coupling includes a series of lenses including a series of filters. Suitable lenses provide an optical magnification of 1× to 100×, and most preferably 10×-40×. Suitable filters can block all or a portion of excitation light and pass all or a portion of emitted light. The illuminator and detection optical paths are suitably coincident between a dichroic filter and the assay device.

Suitable illuminators can be adjacently secured to the sample preparation device to provide a source of excitation to the analyte molecules situated in the assay device. Typical illumination trains include one or more of the following: emission source, apertures, filter sets, and focusing optics. Suitable emission sources can be secured to a filter block and the light can be modified by an aperture. Suitable illumination sources typically include a light emitting diode (LED), a laser, an incandescent light source, a fluorescent light source, an electroluminescent light source, a plasma light source, a laser, or any combination thereof. In certain preferred embodiments of the present invention, the illuminator includes an LED or laser. Suitable LEDs or lasers are capable of emitting any of a variety of light wavelengths. Any variety of two or more light sources can be combined to provide further wavelength distribution to mix colors. For example, light sources can be combined using a split fiber optic bundle connected to two LEDs, lasers, or any combination thereof.

After the device and internal reagents have been illuminated with an excitation source, any emission is detected. Suitable detectors are typically adjacent or optically connected to the device. Typical detection trains can include an excitation source (from analytes or molecules), apertures, filter sets, collection optics, and a suitable photon detector. The selection of the photon detector used allows for different types of detection. Examples of suitable photon detectors include photomultiplier tubes (PMT), avalanche photodiodes (APD), and charge coupled devices (CCD).

Thermal Control of Array for Template Conversion to cDNA

The thermal control of the system allows for performance of standard assay methods as well as new and novel assay investigations. The temperature controller is included to control the temperature of the device before and during the detection. The temperature controller may be in direct or indirect physical contact with the device or it may be in radiative thermal contact with the device. As used herein, "indirect contact" means that at least one other material is situated between the temperature controller and device, e.g. a plate or film. Temperature control can be achieved through a variety of methods, but not limited to: thermoelectric cooler (TEC), resistive heating, evaporative cooling, heat transfer fluids, or other refrigeration systems, and the like. A preferred method of temperature control is the use of a TEC.

For precise temperature control, it is preferable that the TEC be in close contact with the assay device so that the heating or cooling is achieved in a short period of time. Most typically, the controller is capable of regulating the temperature of the device in the range of from about −25 deg. C. to about 150 deg. C. Controlling the temperature of the device is typically used for thermal reduction in device separations, and precise thermal control during nucleic acid interactions and hybridizations.

Control of temperature in distinct regions of the assay device assists in performing and optimizing chemical reactions. For example, between 1-1000 distinct regions of the assay device can be controlled in this capacity. More typically, the number of temperature control regions is in the range of from about 1 to about 10. Control of the temperature can be achieved by using thermistors, which measure the temperature by changes in voltage.

In certain embodiments of the present invention, the system further includes pressure control of the assay device. Suitable pressure controllers can include: syringe pumps, electrokinetic pumps, fluid flow pressure restrictions, or any combination thereof. The pressure control can be directly connected with the device. In some instances, the pressure can also be controlled through the pneumatic control of a distinct region. Most typically, the pressure control is capable of regulating the pressure from 0-32 atmospheres or 0-300 psi.

In various embodiments in the present invention, there are also provided methods that include providing a system of the present invention, thermally controlling a fluidic device, and detecting at least one fluorescent molecule.

The detection systems of the present invention need not only control the temperature, but may also control other variables such as pressure, dynamic flow, and buffer combinations on a single probe. As stated above, the temperature is controlled during hybridization, but the other factors may also be adjusted to optimize hybridization kinetics. Further optimization by one of ordinary skill can be undertaken to minimize reagent use. Working in microfluidic systems helps reduce the amount of reagent used, as compared to standard flat glass arrays and PCR assays. The devices and methods of the present invention make it possible to screen, capture and detect probes in series for optimal conditions.

Nucleic Acid Hybridization

Efficient hybridization of nucleic acids incorporates precise thermal control of the fluids. A nucleic acid ("NA") sample is first denatured to open up its strands in preparation for hybridization. Preventing non-specific hybridization utilizing tight control of the temperature, e.g., a change of 10 degrees Celsius will allow a 1 base mismatch in a 20-base probe. As the detection probe is increased in length, the temperature difference for a mismatch decreases, and the chance of nonspecific hybridization increases.

One application of the system of the present invention is nucleic acid (NA) capture and copying. NA hybridization can be done with an array-bound probe and a sample. The probe can be a set length oligonucleotide or chain of NA bases. Typically, the probe length is 12-1000 bases long. Typically, as many as 6,000,000 probes are used for sample template hybrid capture. The sample is taken from a biological specimen including but not limited to: viruses, bacteria, tissue, blood, animal cells, and plant matter. The length of the sample NA is typically not tightly controlled and may vary from single base pairs up to full length gene sequences. Through sample preparation some control of the NA is possible, often this is a range of 20-10,000 bases. If the sample is longer than 500 bases long, longer incubation times may be required to allow denature and hybridization of the sample template and surface bound primer. This will only be the case for double stranded targets and does not affect the hybridization of single stranded RNA templates and barcoded DNA sample templates.

Probes can be used in two possible ways, first in solution where they interact with the sample NA through diffusion and are dispersed throughout the sample. Secondly, probes can be attached to a fixed surface where the sample NA is allowed to come in contact with the probe. In either case, the temperature of the probe and sample NA in solution is carefully controlled to provide hybridization while limiting non-specific template:primer or primer:primer interaction. The inventive systems of the present invention can be used for optimization of either fixed of free floating probes. Different probes can open up at different temperatures, which is dependent on the bases associated with the probe and anything that is connected with the probe, such as chemistry for connecting to a fixed surface or fluorescent probes. The temperature for conducting proper hybridization is preferably determined.

Device Electrophoresis

Device electrophoresis can be performed by applying a voltage or current from an anode to cathode that are connected via a microfluidic channel or device. This voltage potential results in migration of charged species or colloidal particles, which migration causes the movement of ions through the chamber. The speed of the migration, i.e., separation, depends on the current across the separation chamber. As the current is increased, the separation takes a shorter time. The limiting factor for separation velocity is the resulting joule heating generated with high current flows. As heat is generated in the device, bubbles form at high temperature points. The bubbles act as dielectrics and force the current through a smaller path which generates higher temperatures. By cooling the separation chamber, heat generated during the separation is removed and higher voltages can be used, resulting in faster separations.

Device cooling also increases resolution of the separation. The resolution of the sample is limited by the diffusion of the sample. The sample will naturally diffuse in the chamber. There are two ways to limit the diffusion of the sample during a separation. The first is to complete the separation in a shorter time, reducing the time for diffusion to take place. The second is to decrease the temperature of the sample, which effectively slows diffusion.

By reducing and controlling the temperature of the electrophoretic separation, higher voltages can be used and diffusion can be limited. In the process of modifying the temperature, the ability of the nucleic acid to properly base pair can be effected. As the temperature decreases, more non-specific hybridization occur due to secondary structure formation of the template and primer structures. Alternatively, in certain embodiments, such as a primer that is hybridized to a covalently linked array oligonucleotide, increases in temperature can cause melting or denaturing of this hybrid primer:array oligo complex. As result careful method development of temperature control of the array structure is important and requires active control to ensure proper template:primer hybridization.

Temperature control for electrophoresis can also allow the use of alternate sieving materials, especially materials that would be affected by fluctuations in temperature. Specific control of distinct regions can also allow some sample preparation to be performed in the separation channel. For example, in DNA separations, the sample can be denatured just before entering the sieving matrix. The detection systems of the present invention allow for new and novel techniques in separation technologies.

Illustrative Embodiments

The following embodiments are illustrative only and do not limit the scope of the present disclosure or the appended claims.

EXAMPLES

The following examples are illustrative only and do not limit the scope of the present disclosure or the appended claims.

Embodiment 1. A system, comprising: a plurality of base polynucleotides disposed on an amplification substrate; an optionally porous cellular support substrate, the optionally porous cellular support substrate and the amplification substrate defining a chamber therebetween; an inlet, the inlet optionally comprising an aperture formed in the cover, the inlet optionally placing the optionally porous layer into fluid communication with the environment exterior to the optionally porous cellular support substrate.

Embodiment 2. The system of embodiment 1, further comprising a frame disposed between the amplification substrate and the optionally porous cellular support substrate, the frame defining the chamber between the optionally porous cellular support substrate and the amplification substrate.

Embodiment 3. The system of any of embodiments 1-2, wherein one or both of the substrate and the optionally porous cellular support substrate is a conductive material.

Embodiment 4. The system of any of embodiments 1-3, further comprising a voltage source configured to supply an electrical gradient between the optionally porous cellular support substrate and the substrate, the electrical gradient being configured so as to translocate nucleic acids in a direction essentially perpendicular to the optionally porous cellular support substrate and toward the amplification substrate.

Embodiment 5. The system of any of embodiments 1-4, further comprising an imager in optical communication with the chamber.

Embodiment 6. The system of any of embodiments 1-5, further comprising a source of reagents in fluid communication with the inlet.

Embodiment 7. The system of any of embodiments 1-6, wherein the plurality of base polynucleotides is disposed on two or more discrete regions of the amplification substrate.

Embodiment 8. The system of any of embodiments 1-7, wherein at least some of the base polynucleotides of the amplification substrate are bound to amplification primers.

Embodiment 9. The system of embodiment 8, wherein at least some of the amplification primers comprise one or more of (1) a nucleic acid sequence complementary to one or more base polynucleotides of the amplification substrate, (2) a nucleic acid sequence associated with the location of the amplification primer on the amplification substrate, (3) a nucleic acid sequence specific to that amplification primer, and (4) a nucleic acid sequence complementary to a target nucleic acid sequence in a sample.

Embodiment 10. The system of embodiment 9, wherein at least some of the amplification primers comprise at least two nucleic acid sequences associated with the location of the amplification primer on the amplification substrate.

Embodiment 11. The system of any of embodiments 9-10, wherein at least some of the amplification primers comprise at least (1) a nucleic acid sequence complementary to one or more base polynucleotides of the amplification substrate, (2) a nucleic acid sequence associated with the location of the amplification primer on the amplification substrate, (3) a nucleic acid sequence specific to that amplification primer, and (4) a nucleic acid sequence complementary to a target nucleic acid sequence in a sample.

Embodiment 12. A method, comprising: liberating nucleic acids from a cellular sample affixed to an optionally porous cellular support substrate, the cellular sample being capable of fluid communication with an amplification substrate bearing a plurality of amplification primers; translocating the liberated nucleic acids in a direction essentially perpendicular from the optionally porous cellular support substrate under such conditions that the liberated nucleic acids hybridize to the plurality of amplification primers, the liberated nucleic acids optionally being communicated in the direction of the plurality of amplification primers through the pores of a porous material; and amplifying the nucleic acids so as to give rise to amplification products.

Embodiment 13. The method of embodiment 12, wherein the translocating is effected by a voltage gradient.

Embodiment 14. The method of any of embodiments 12-13, wherein the liberating is effected by one or more reagents contacted to a porous substrate in fluid communication with the cellular sample.

Embodiment 15. The method of embodiment 14, wherein the substrate is a porous substrate.

Embodiment 16. The method of any of embodiments 12-15, wherein the cellular sample contacts the amplification substrate.

Embodiment 17. The method of any of embodiments 12-16, further comprising collecting the amplification products.

Embodiment 18. The method of any of embodiments 12-17, wherein at least some of the amplification primers comprise one or more of (1) a nucleic acid sequence complementary to one or more base polynucleotides of the amplification substrate, (2) a nucleic acid sequence associated with the location of the amplification primer on the amplification substrate, (3) a nucleic acid sequence specific to that amplification primer, and (4) a nucleic acid sequence complementary to a target nucleic acid sequence in a sample.

Embodiment 19. The method of any of embodiments 12-18, further comprising associating an amplification product with a location within the cellular sample.

Embodiment 20. The method of any of embodiments 12-19, further comprising associating an amplification product with an amplification primer.

Embodiment 21. The method of any of embodiments 12-20, further comprising affixing the cellular sample to the optionally porous cellular support substrate.

Embodiment 22. The method of any of embodiments 12-21, further comprising removal of one or more fixatives from the cellular sample.

Embodiment 23. The method of any of embodiments 12-22, further comprising hybridizing the amplification primers to base polynucleotides affixed to the amplification substrate.

Embodiment 24. A method, comprising: liberating nucleic acids from a cellular sample affixed to an optionally porous cellular support substrate, the cellular sample overlying a plurality of amplification primers; translocating the nucleic acids in a direction perpendicular from the optionally porous cellular support substrate under such conditions that the nucleic acids hybridize to at least some of the plurality of amplification primers, the liberated nucleic acids optionally being communicated in the direction of the plurality of amplification primers through the pores of a porous material; amplifying the nucleic acids so as to give rise to amplification products; and associating at least some of the amplification products with locations within the cellular sample.

Embodiment 25. The method of embodiment 24, wherein the liberating is effected by one or more reagents contacted to a porous substrate in fluid communication with the cellular sample.

Embodiment 26. The method of embodiment 25, wherein the porous substrate is the optionally porous cellular support substrate.

Embodiment 27. A sample preparation system for high resolution spatial genetic analysis, comprising: (a) a sample preparation module material capable of attaching a cellular sample to an optionally porous cellular support substrate that allows imaging of the tissue or cell aggregate or tissue section sample on one side, and provides the ability to deliver reagents to the sample; (b) a sample preparation module material that allows chemical fixation of a cellular sample to occur on the surface of the optionally porous cellular support substrate; (c) a sample preparation module that is chemically inert to non-polar solvents; (d) a sample preparation module capable of treating the cellular sample treated with reagents to label proteins with nucleic acid sequenced tagged antibodies, aptamers or any other ligand to bind to a specific protein with a cell in the sample; (e) a device capable of imaging of the cellular sample in close proximity to an array of oligonucleotides to coordinate the tissue sample location with each oligonucleotide element on the array; (f) a sample preparation module that seals the integrated device so as to prevent lateral fluid flow during migration of the target nucleic acids and so as to effect fluid flow over a bar-coded array of oligonucleotides; (g) a module by which samples are digested with proteolytic enzymes, including but not limited to proteinase or protease to release one or more sample templates; (h) a module that effects migration of charged nucleic acid templates to the array surface in an x-y plane such that (i) the process of (f) is effected such that sample templates are migrated under the control of electrophoresis and/or (ii) the process of (f) is effected so samples migrate to the array surface under the control of z-directional flow generated by pressure of electrokinetic flow; (i) at least 20,000 oligonucleotide probes on the array, (i) optionally in the array, the areal density of probes being equal to or greater than the density of the areal density of cells that reside on the optionally porous cellular support substrate, (ii) at least some of the oligonucleotide probes comprising a set of first array sequences that in combination with a second set of barcode sequences form a hybrid pair with the 3' end exposed so as to serve as a hybridization and primer element on the array, (iii) at least some of the set of first array sequences being synthesized in reverse order with the 3' end exposed that serves as a hybridization and primer element on the array, (iv) a set of array sequences that contain a primer sequence on the 3' terminus, which may include an oligo dT sequence, a specific primer sequence, or a random sequence, (v) a plurality of oligonucleotide probes that include a sequence that effects quantification of the copy number of sample template molecules, (vi) a plurality of probe elements that comprise a plurality of barcoded oligonucleotides associated with the location, presence, or both of a genetic element specific to a cell, a cell region, regions or the entire array, (vii) a barcode array that comprises a number of distinct barcode sequences that allow amplification or enrichment of a selected area on the array, (j) the system being configured such that one or more reactions can be conducted on the array surface, the one or more reactions comprising the use of one or more of a RNA or DNA dependent DNA polymerase, a ligase, exonuclease, or endonuclease so as to provide the ability to create a barcoded first strand cDNA, (k) the system being configured so as to allow first strand reaction products to be released from the surface using a restriction endonuclease or temperature to release the first strand cDNA, (l) the system being configured so as to allow a process that provides a sample that can be transformed into a sequencing library with known barcode sequences which can be split into individual reactions to provide a sample that is sequenced at high read depth using next generation sequencing.

Embodiment 28. A fluidic device to perform high resolution spatial genomic analysis, comprising: a sample preparation module, a series of fluidic channels and an array of oligonucleotides disposed on a conductive surface within the device so as to allow for one or more of sample addition, fixation, paraffin removal, incubation, sample imaging, active control target of sample nucleic acid templates, and multistep molecular biology reactions to effect sample preparation, hybridization, reverse transcription and first strand cDNA synthesis of sample templates with the device.

Embodiment 29. The device of embodiment 28, further comprising sample preparation module material that effects attaching the sample to a cellular support substrate, the cellular support substrate optionally being porous, and the material further allowing imaging of the tissue or cell aggregate or tissue section sample on one side of the optionally porous cellular support membrane and providing the ability to deliver reagents to the sample.

Embodiment 30. The device of any of embodiments 28-29, wherein the sample preparation module material that allows the attaching to occur resides on the conductive surface.

Embodiment 31. The device of any of embodiments 28-30, wherein the sample preparation module is chemically inert to non-polar solvents.

Embodiment 32. The device of any of embodiments 28-31, wherein the sample preparation module allows the sample to be treated with reagents to label proteins with nucleic acid sequenced tagged antibodies, aptamers or any other ligand to bind to a specific protein with a cell in the sample.

Embodiment 33. The device of any of embodiments 28-32, wherein the device allows for an image of the combined sample in close proximity to an array of oligonucleotides to coordinate the tissue sample location with each oligonucleotide element on the array.

Embodiment 34. The device of any of embodiments 28-33, wherein the sample preparation module seals the integrated device so as to prevent lateral fluid flow during migration of the target nucleic acids and so as to allow controlled lateral fluid flow over a bar-coded array of oligonucleotides.

Embodiment 35. The device of any of embodiments 28-34, further comprising a module whereby samples are digested with a proteolytic enzyme, including but not limited to proteinase or protease to release one or more sample templates.

Embodiment 36. The device of any of embodiments 28-35, further comprising a module that effects migration of the charged nucleic acid templates to the array surface.

Embodiment 37. The device of any of embodiments 28-36, further comprising a module whereby sample templates are migrated under the control of electrophoresis.

Embodiment 38. The device of any of embodiments 28-37, further comprising a process where cellular samples templates are migrated under the control of directional flow generated by pressure of electrokinetic flow.

Embodiment 39. The device of embodiment 38, wherein the areal density of probe elements in the array is equal or higher than the density of the cells which reside on the cellular support substrate.

Embodiment 40. The device of any of embodiments 28-39, wherein the array comprises from about 3000 to about 2,000,000 oligonucleotide probe array elements.

Embodiment 41. The device of any of embodiments 28-40, wherein the array comprises a set of oligonucleotide probe elements comprising first array sequences that in combination with a set of barcode sequences form a hybrid pair with the 3' end exposed that serves as a hybridization and primer element on the array.

Embodiment 42. The device of any of embodiments 28-41, wherein the array comprises a set of first array sequences that are synthesized in high density in reverse order with the 3' end exposed that serves as a hybridization and primer element on the array.

Embodiment 43. The device of any of embodiments 28-42, wherein the array comprises a set of array sequences that contain a primer sequence on the 3' terminus, which may include an oligo dT sequence, a specific primer sequence or a random sequence.

Embodiment 44. The device of any of embodiments 28-43, further comprising a plurality of oligonucleotide probes that comprise a sequence that allow accurate quantification of the copy number of sample template molecules.

Embodiment 45. The device of any of embodiments 28-44, further comprising a plurality of probe elements associated with the location, presence, or both of a genetic element specific to a cell, a cell region, regions or the entire array.

Embodiment 46. The device of any of embodiments 28-45, further comprising a barcode array that comprises a number of distinct barcode sequences that allows amplification or enrichment of a selected area on the array.

Embodiment 47. The device of any of embodiments 28-46, the device being configured such that one or more reactions can be conducted on the array surface, the one or more reactions comprising the use of one or more of a RNA or DNA dependent DNA polymerase, a ligase, exonuclease, or endonuclease so as to provide the ability to create a barcoded first strand cDNA.

Embodiment 48. The device of any of embodiments 28-47, the device being configured to allow the first strand reaction products to be released from the surface using a restriction endonuclease or temperature to release the first strand cDNA.

Embodiment 49. The device of any of embodiments 28-48, the device being configured so as to allow a process that provides a sample that can be transformed into a sequencing library with known barcode sequences which can be split into individual reactions to provide a sample that is sequenced at high read depth using next generation sequencing.

Embodiment 50. A method for spatially resolving protein and/or nucleic acids from biological samples, comprising the steps of: mounting a sample to a porous surface; hydrating the sample; placing the sample into fluid communication with a second surface that having a barcode disposed thereon and the second surface being electrically conductive; obtaining positional information regarding the sample relative to the barcode array; digesting the sample so as to release nucleic acid targets; translocating the targets to the barcode array of the second surface so as to effect hybridization; effecting sequencing of the hybridized targets; correlating results of the sequencing so as to positionally resolve the location within the sample from which one or more targets originated.

Embodiment 51. The method of embodiment 50, wherein the sample is one or more of a cellular monolayer and a formalin-fixed paraffin embedded sample.

Embodiment 52. The method of any of embodiments 50-51, wherein the barcode array is (a) permanently fixed to the second surface; or (b) releasable from the second surface by endonuclease activity or temperature.

Embodiment 53. The method of any of embodiments 50-52, wherein the number of array elements is at least 3,000, and preferably at least 20,000.

Embodiment 54. The method of any of embodiments 50-53, wherein the translocating is effected by electrophoresis.

Embodiment 55. The method of any of embodiments 50-54, wherein the translocation is electrokinetically induced.

56. The method of any of embodiments 50-55, wherein the probes comprise one or more of (a) a sequence that allows for quantification of the copy number of sample template and (b) a sequence that allows for enrichment of a specific area of the array.

Embodiment 57. The method of any of embodiments 50-56, further comprising performing one or more reactions on the array surface, one or more of the reactions includes the use of a RNA or DNA dependent DNA polymerase, a ligase, exonuclease, endonuclease to provide the ability to create a barcoded first strand cDNA.

In one illustrative embodiment of the disclosed technology, a cellular sample (e.g., a cellular monolayer, an FFPE sample, or other sample) is affixed to a "front" surface of a cellular support substrate. This affixation may be accomplished in a variety of ways that will be known to those of skill in the art. The cellular support substrate may be porous, although this is not a requirement. The cellular support substrate may be conductive in nature, although this too is not a requirement. In some embodiments that feature a porous cellular support substrate, reagents—e.g., lysing reagents, buffers, and the like—may be introduced to the "back" surface of the cellular support substrate so as to then contact the cellular sample. The reagents may be introduced by way of an aperture formed in a cover, the aperture being in fluid communication with the porous cellular support substrate.

The cellular support substrate (and cellular sample) may be disposed across from an amplification substrate, which amplification substrate may comprise an array of oligonucleotide probes, as shown in one or more of FIGS. 3, 4, 8, and 9. The amplification substrate may be conductive in nature, as shown in FIG. 1. A device may include an input inlet and, optionally, an output outlet. The input inlet may allow introduction of reagents, washes, and the like, and the output outlet may allow for the output of washes, buffers, excess reagents, and even reaction products. As shown in FIG. 1, a device according to the present disclosure may include a reagent electrode inlet, which may be used to introduce reagents to a cellular sample; this is particularly suitable when the cellular sample is fixed to a porous cellular support substrate.

FIG. 2 provides an exploded view of a device according to the present disclosure. As shown in FIG. 2, a device may include a high density barcode array (of oligonucleotides); such arrays are described elsewhere herein in additional detail. The barcode array may be formed on a substrate material, which substrate material may be conductive.

A device may include a channel layer (optionally adhesive in nature). As shown, the channel layer may define tapered regions and/or regions of constant cross section.

Also present may be a fluidic interconnect. As shown, an interconnect may include one or more apertures formed therein, which apertures may be used as inlets and/or outlets as shown in FIG. 1.

As shown in FIG. 2, a device may include a porous substrate useful for cellular support, although this substrate need not necessarily be porous, although a porous substrate is considered especially suitable. As described elsewhere herein, a cellular sample may be fixed to the (optionally) porous substrate. The device may include an adhesive layer, a gasket (which may be characterized as an O-ring), an additional adhesive layer, and even a compression frame. As shown, the compression frame (sometimes termed "cover") may include an aperture formed therethrough, which aperture may place a cellular sample fixed to a porous layer into fluid communication with the environment exterior to the compression frame. It should be understood that a device according to the present disclosure may also include a porous material (not shown) disposed between the optionally porous cellular support substrate and the substrate that comprises the barcode array. This porous material may be considered a "guiding material" and may comprise a plurality of channels that allow for transport of material from a cellular sample on the cellular support substrate directly toward the array, with the pores acting to minimize diffusion and/or movement of material in directions that are not directly toward the array. Put another way, the porous material may act to enhance transport of material (e.g., liberated nucleic acids) in a direction perpendicular from the cellular support substrate towards the barcode array.

For example, if a cell resides directly above the four central (i.e., 2×2 set) probes in a 4×4 array of probes, placing a porous material between the cell and the 4×4 array of probes will improve the transport of material that is liberated from the cell directly to the 2×2 probes directly underneath the cell and reduce the amount of liberated cellular material that might be transported to probes that encircle the central 2×2 set of probes in the 4×4 array. The porous material may be characterized as having channels formed therein. Capillary sheets and the like are considered suitable porous (or "guiding") materials; a guiding material suitably has discrete pores or channels that are parallel to one another and run perpendicular to the surface(s) of the material.

FIG. 5 illustrates a device according to the present disclosure. FIG. 5A illustrates a porous cellular support substrate engaged with an O-ring sealing gasket, and FIG. 5B illustrates a compression frame having an inlet through hole formed therein. A tissue section (FIG. 5C) may be fixed to the cellular support layer, and then, as shown in FIG. 5D, the tissue section is present in the chamber defined between the various device layers shown in FIGS. 1 and 2, the tissue section now being available for treatment by reagents, buffers, and the like that are introduced from external to the chamber. FIG. 7 illustrates a cutaway view of a device according to the present disclosure, illustrating (via the arrows) how material (e.g., reagents, buffers, and the like) delivered through the through-hole of the cover may then become distributed along the porous cellular support substrate and as a consequence to cells that are fixed to or otherwise associated with that substrate. FIG. 6 (described elsewhere herein) depicts, from top to bottom, an exemplary process according to the present disclosure.

Figure 3:
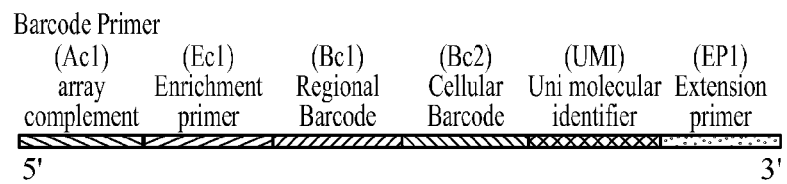
FIG. 3 provides an exemplary embodiment of a single barcoded oligonucleotide that is hybridized to a specific group of oligonucleotides deposited on the array surface that is attached to a surface which contains a conductive layer. This barcode primer oligonucleotide contains various regions: (AC1) an array complement sequence, an enrichment primer sequence (Ed), a regional barcode sequence (BC1), a probe specific barcode sequences (BC2), a unique-molecular identifier (UMI) which is a random sequence placed into an individual oligonucleotide, and an extension primer (EP1) which acts as a primer to perform the cDNA first strand synthesis. It should be understood that this FIG. is illustrative of only a single barcoded oligonucleotide and that other barcoded oligonucleotides may include sequences (e.g., Ac2, Ec2, Bc5, Bc6, EP2, and a different UMI).
Figure 3:
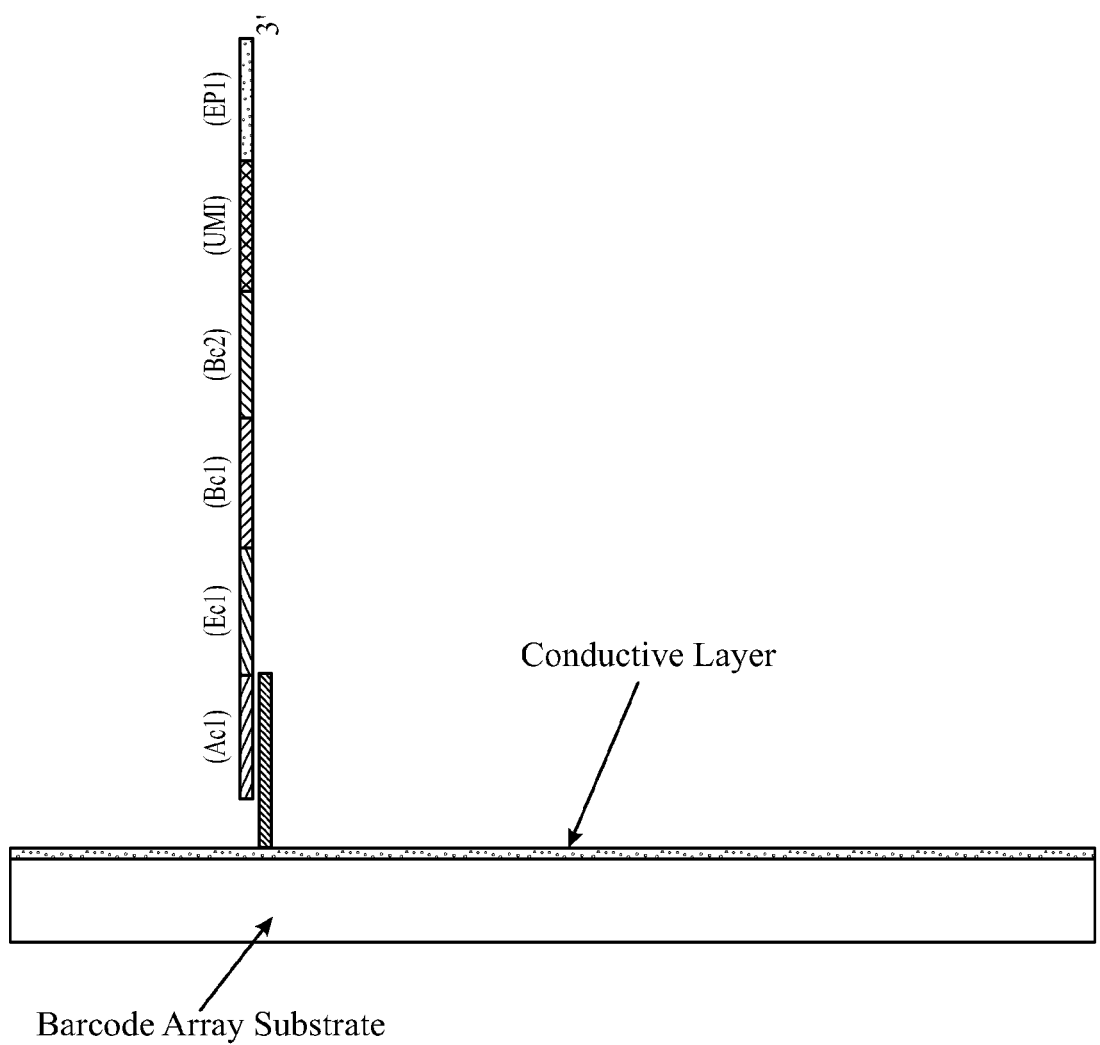

As shown, a barcode array may comprise one or more probes according to the example of FIG. 3. It should be understood that—as described elsewhere herein—a given probe may include one or more sequences that provide specific information regarding the location of the probe (e.g., the probe's relative location within the array), regarding a cellular sample (including a cell of the cellular sample) that may be associated with the probe, regarding a specific molecule (e.g., information regarding a cell, a gene, a treatment, a disease state, and the like), or even other information regarding that given probe. By amplifying the hybridization product of a given probe with a given nucleic acid liberated from a cell or even a region of a cell, a user can then determine a variety of location-specific characteristics of the liberated nucleic acid. (Suitable hybridization, amplification, and other steps are shown in FIGS. 4, 6, 8, and 9.

For example, a user may determine that in a tissue sample of a cross-section of a liver, a cell at locations $X_{1-100}$, $Y_{1-100}$ may possess a certain gene of concern, whereas cells at locations $X_{101-1000}$, $Y_{101-1000}$ do not possess that same gene of concern. This may in turn allow for an improved treatment recommendation that involves excision of tissue at only the locations where the gene of concern was present, instead of total excision of the liver.

EXAMPLES

Example 1

Analysis of an FFPE Section

In one embodiment, a device is used to identify the transcribed genes and expressed proteins of a particular group of cells at single cell resolution from an FFPE section.

In one example, a user mounts a 4-20 micrometer section of tissue to a customized sample transfer slide and heats this slide for approximately 1-3 hours to attach the sample material to the slide. The paraffin that surrounds the sample is removed from the transfer device.

The sample, now attached to the transfer device can be exposed to a variety of reagents including antibodies (which include an oligonucleotide to identify the specific antibody) to detect expressed proteins. This slide is then incubated to allow hybridization of the oligo linked antibodies to the proteins on the cells within the tissue sample.

After a series of washes to remove non-specifically hybridized antibodies, the transfer device is assembled with the array cartridge. The assembled device is then imaged using a standard epi-fluorescent microscope. Reagents to conduct the sample permeabilization and first strand cDNA production are loaded into the cartridge. The user then inserts the cartridge into the instrument to conduct the automated permeabilization, template hybridization, and first strand synthesis reaction. The device in a series of steps introduces the permeabilization reagents, and controls the temperature to conduct this digestion. In parallel, the device activates the electric field to conduct electrophoresis of the sample templates, now being liberated from the sample (including the oligonucleotides that are attached to the antibodies), to the high density array, which either contains an array of covalently linked primers (with the 3' end exposed) or an array of 3' attached oligonucleotides with a second complexed primer. Using this electrophoretic mode, the sample templates hybridize to the array surface.

When hybridization is complete the array is washed and the array, with the hybridized templates complexed to the array, is exposed to the reagents required for reverse transcriptase. These reagents are then incubated in the chamber, which extends the primers that are hybridized to the sample templates. When this reaction is complete, the extended first strand cDNA products are then released from the high density array either through the use of a restriction enzyme, or denaturation or both. The released first strand cDNAs are then exported to an outlet well on the cartridge, where the user removes this material by aspiration with a pipette. This sample is then purified using magnetic beads, and then subjected to a ligation protocol to add the 5' oligonucleotide to the first strand cDNA. The sample is once again purified, and prepared for enrichment.

To perform enrichment of target region, the user first returns to the sample image, and through the software system selects the regions of interest within the image. These regions of interest correspond set of barcodes which are used as primers during the enrichment process. The user then selects tis set of primer from a plate of barcode primers and combines this with the purified sample eluted from the device. The combination is then thermal cycled to amplify the regions of interest corresponding to the original image. Due to the structure of the barcode primers the product of this reaction is sequencer-ready once re-purified. Each regional barcode selected by the user may contain approximately 1000 cells. Approximately 3-6 regions can be submitted to the single sequencing lane, using a standard flow cell sequencing system (e.g., Illumina™ systems) depending on the sequencing depth required by the user. As each sequencing flow cell contains eight lanes, the user may analyze up to 50,000 cells per sequencing run. The user re-use the sample to produce more enriched regions for sequencing, even every cell (e.g., millions of cells) in the image. With sequencing analysis complete the user compiles the BML or FASTQ file with the cell image to create a series of heat maps to identify the genes that variable between the cells with the region of interest. This process effectively links the cell morphology and phenotype to the underlying genetic and proteomic structure.

Example 2

Analysis of a Cell Suspension

The disclosed technology may be used to identify the transcribed genes and expressed proteins of a particular group of cells at single cell resolution from a cell suspension. In this example performs a procedure known as "cytospin" to affix suspension cells of interest to a customized sample transfer slide. The sample is then preserved using a fixation procedure, which may include paraformaldehyde, glutaldehyde, an alcohol or a combination thereof. The sample, now attached to the transfer device can be exposed to a variety of reagents including antibodies (which include an oligonucleotide to identify the specific antibody) to detect expressed proteins. This slide is then incubated to allow hybridization of the oligo linked antibodies to the proteins on the cells within the tissue sample.

After a series of washes to remove non-specifically hybridized antibodies, the transfer device is assembled with the array cartridge. The assembled device is then imaged using a standard epi-fluorescent microscope. Reagents to conduct the sample permeabilization and first strand cDNA production are loaded into the cartridge. The user then inserts the cartridge into the instrument to conduct the automated permeabilization, template hybridization, and first strand synthesis reaction. The device in a series of steps introduces the permeabilization reagents, and controls the temperature to conduct this digestion. In parallel, the device activates the electric field to conduct electrophoresis of the sample templates, now being liberated from the sample (including the oligonucleotides that are attached to the antibodies), to the high density array, which either contains an array of covalently linked primers (with the 3' end exposed) or an array of 3' attached oligonucleotides with a second complexed primer. Using this electrophoretic mode, the sample templates hybridize to the array surface.

When hybridization is complete the array is washed and the array, with the hybridized templates complexed to the array, is exposed to the reagents required for reverse transcriptase. These reagents are then incubated in the chamber, which extends the primers that are hybridized to the sample templates. When this reaction is complete, the extended first strand cDNA products are then released from the high density array either through the use of a restriction enzyme, or denaturation or both. The released first strand cDNAs are then exported to an outlet well on the cartridge, where the user removes this material by aspiration with a pipette. This sample is then purified using magnetic beads, and then subjected to a ligation protocol to add the 5' oligonucleotide to the first strand cDNA. The sample is once again purified, and prepared for enrichment.

To perform enrichment of target region, the user first returns to the sample image, and through the software system selects the regions of interest within the image. These regions of interest correspond set of barcodes which are used as primers during the enrichment process. The user then selects tis set of primer from a plate of barcode primers and combines this with the purified sample eluted from the device. The combination is then thermal cycled to amplify the regions of interest corresponding to the original image. Due to the structure of the barcode primers the product of this reaction is sequencer-ready once re-purified. Each regional barcode selected by the user will contain approximately 1000 cells. Approximately 3-6 regions can be submitted to the single sequencing lane, using a standard flow cell sequencing system (e.g., an Illumina™ system) depending on the sequencing depth required by the user. As each sequencing flow cell contains eight lanes, the user can analyze up to 50,000 cells per sequencing run. The user re-use the sample to produce more enriched regions for sequencing, even every cell (e.g., millions of cells) in the image. With sequencing analysis complete the user compiles the BML of FASTQ file with the cell image to create a series of heat maps to identify the genes that variable between the cells with the region of interest. This process effectively links the cell morphology and phenotype to the underlying genetic and proteomic structure.

At least some of the following documents are mentioned above (by bracketed references) in the present disclosure; all of the following documents are incorporated herein by reference in their entireties for any and all purposes:

1. Hrdlickova, R., M. Toloue, and B. Tian, RNA-Seq methods for transcriptome analysis. Wiley Interdiscip Rev RNA, 2016.
2. Fuller, C. W., et al., The challenges of sequencing by synthesis. Nat Biotechnol, 2009. 27(11): p. 1013-23.
3. Madabusi, L. V., G. J. Latham, and B. F. Andruss, RNA extraction for arrays. Methods Enzymol, 2006. 411: p. 1-b 14.
4. Shalek, A. K., et al., Single-cell RNA-seq reveals dynamic paracrine control of cellular variation. Nature, 2014. 510 (7505): p. 363-9.
5. Pollen, A. A., et al., Low-coverage single-cell mRNA sequencing reveals cellular heterogeneity and activated signaling pathways in developing cerebral cortex. Nat Biotechnol, 2014. 32(10): p. 1053-8.
6. Pollen, A. A., et al., Molecular identity of human outer radial glia during cortical development. Cell, 2015. 163 (1): p. 55-67.
7. Gawad, C., W. Koh, and S. R. Quake, Dissecting the clonal origins of childhood acute lymphoblastic leukemia by single-cell genomics. Proc Natl Acad Sci USA, 2014. 111(50): p. 17947-52.
8. Gong, H., et al., Simple Method To Prepare Oligonucleotide-Conjugated Antibodies and Its Application in Multiplex Protein Detection in Single Cells. Bioconjug Chem, 2016. 27(1): p. 217-25.
9. Genshaft, A. S., et al., Multiplexed, targeted profiling of single-cell proteomes and transcriptomes in a single reaction. Genome Biol, 2016. 17(1): p. 188.
10. Crosetto, N., M. Bienko, and A. van Oudenaarden, Spatially resolved transcriptomics and beyond. Nat Rev Genet, 2015. 16(1): p. 57-66.
11. Stahl, P. L., et al., Visualization and analysis of gene expression in tissue sections by spatial transcriptomics. Science, 2016. 353(6294): p. 78-82.
12. Jiang, C. Y., et al., High-Throughput Single-Cell Cultivation on Microfluidic Streak Plates. Appl Environ Microbiol, 2016. 82(7): p. 2210-8.
13. Macosko, E. Z., et al., Highly Parallel Genome-wide Expression Profiling of Individual Cells Using Nanoliter Droplets. Cell, 2015. 161(5): p. 1202-14.
14. Hoover, M., et al., A novel method for RNA extraction from FFPE samples reveals significant differences in biomarker expression between orthotopic and subcutaneous pancreatic cancer patient-derived xenografts. Oncotarget, 2016.
15. Hedegaard, J., et al., Next-generation sequencing of RNA and DNA isolated from paired fresh-frozen and formalin-fixed paraffin-embedded samples of human cancer and normal tissue. PLoS One, 2014. 9(5): p. e98187.
16. Fan, H. C., G. K. Fu, and S. P. Fodor, Expression profiling. Combinatorial labeling of single cells for gene expression cytometry. Science, 2015. 347(6222): p. 1258367.
17. Karlsson, K., et al., Amplification-free sequencing of cell-free DNA for prenatal non-invasive diagnosis of chromosomal aberrations. Genomics, 2015. 105(3): p. 150-8.
18. Myers, T. W. and D. H. Gelfand, Reverse transcription and DNA amplification by a *Thermus thermophilus* DNA polymerase. Biochemistry, 1991. 30(31): p. 7661-6.

19. Auer, T., et al., Selective amplification of RNA utilizing the nucleotide analog dITP and *Thermus thermophilus* DNA polymerase. Nucleic Acids Res, 1996. 24(24): p. 5021-5.
20. Trombetta, J. J., et al., Preparation of Single-Cell RNA-Seq Libraries for Next Generation Sequencing. Curr Protoc Mol Biol, 2014. 107: p. 4221-17.
21. Murray, I. A., S. K. Stickel, and R. J. Roberts, Sequence-specific cleavage of RNA by Type II restriction enzymes. Nucleic Acids Res, 2010. 38(22): p. 8257-68.
22. Fahy, E., D. Y. Kwoh, and T. R. Gingeras, Self-sustained sequence replication (3SR): an isothermal transcription-based amplification system alternative to PCR. PCR Methods Appl, 1991. 1(1): p. 25-33.
23. Uyttendaele, M., et al., Development of NASBA®, a nucleic acid amplification system, for identification of Listeria monocytogenes and comparison to ELISA and a modified FDA method. International Journal of Food Microbiology, 1995. 27(1): p. 77-89.
24. Gulliksen, A., et al., Parallel nanoliter detection of cancer markers using polymer microchips. Lab Chip, 2005. 5(4): p. 416-20.
25. Schena, M., et al., Parallel human genome analysis: microarray-based expression monitoring of 1000 genes. Proc Natl Acad Sci USA, 1996. 93(20): p. 10614-9.
26. Schena, M., et al., Quantitative monitoring of gene expression patterns with a complementary DNA microarray [see comments]. Science, 1995. 270(5235): p. 467-70.
27. Nuwaysir, E. F., et al., Gene expression analysis using oligonucleotide arrays produced by maskless photolithography. Genome Res, 2002. 12(11): p. 1749-55.
28. Chee, M., et al., Accessing genetic information with high-density DNA arrays. Science, 1996. 274(5287): p. 610-4.
29. Albert, T. J., et al., Light-directed 5'→3' synthesis of complex oligonucleotide microarrays. Nucleic Acids Res, 2003. 31(7): p. e35.
30. Gu, G. J., et al., Protein tag-mediated conjugation of oligonucleotides to recombinant affinity binders for proximity ligation. N Biotechnol, 2013. 30(2): p. 144-52.
31. Piepenburg, Olaf; Williams, Colin H.; Stemple, Derek L.; Armes, Niall A. (2006). "DNA Detection Using Recombination Proteins". PLoS Biology. 4 (7): e204. PMC 1475771, PMID 16756388. doi:10.1371/journal.pbio.0040204.
32. Gansauge et al., "Single-Stranded DNA Library Preparation From Highly Degraded DNA Using T4 DNA Ligase", Nucleic Acids Research 2017, vol. 45, No. 10, e79.

What is claimed:
1. A method for spatial analysis comprising:
   (a) providing or obtaining an integrated system comprising:
      (i) a first surface comprising a porous cellular support;
      (ii) a second surface comprising a tile array of barcoded oligonucleotides, wherein the tile array comprises a plurality of regions defined on a plane and a barcoded oligonucleotide of the tile array comprises a regional barcode shared between barcoded oligonucleotides of a first region of the tile array and different among the different regions of the tile array;
      (iii) a chamber defined between the first surface and the second surface comprising a cellular sample affixed to the porous cellular support and in direct fluid communication with the tile array via fluid transport through pores of the porous cellular support; and,
      (iv) one or more electrodes for generating a voltage gradient between the porous cellular support and the tile array of barcoded oligonucleotides for generating perpendicular fluid flow therebetween and through the chamber;
   (b) liberating a nucleic acid molecule from a cell of the cellular sample;
   (c) translocating the liberated nucleic acid in a direction essentially perpendicular to the porous cellular support substrate, through pores of the porous cellular support substrate toward the tile array of barcoded oligonucleotides by applying the voltage gradient;
   (d) hybridizing the liberated nucleic acid to a barcoded oligonucleotide of the tile array, wherein the regional barcode of the barcoded oligonucleotide identifies the region of the cell in the cellular sample;
   (e) amplifying the nucleic acid to generate a plurality of amplification products therefrom; and
   (f) identifying the region of the cell using the regional barcode.

2. The method of claim 1, wherein the integrated system further comprises a through hole for supplying one or more reagents and facilitating access to the one or more electrodes, and wherein the translocating is affected by one or more reagents contacted with the sample via the through hole.

3. The method of claim 1, wherein at least some of the barcoded oligonucleotides comprise:
   (1) a nucleic acid sequence complementary to one or more base polynucleotides of the second surface for binding the barcoded oligonucleotide to the second surface;
   (2) an amplification primer, wherein the amplification primer is capable of amplifying the barcoded oligonucleotide and the liberated nucleic acid;
   (3) a nucleic acid sequence specific to the amplification primer; and,
   (4) a nucleic acid sequence complementary to the liberated nucleic acid.

4. The method of claim 1, further comprising correlating an amplification product of the plurality of amplification products with the region using the second barcode.

5. The method of claim 1, further comprising correlating an amplification product with a barcoded oligonucleotide of the tile array.

6. The method of claim 1, further comprising affixing the cellular sample to the porous cellular support substrate.

7. A method, comprising:
   (a) liberating nucleic acids from a cell in a cellular sample affixed to a porous cellular support substrate in a chamber defined between the cellular support substrate and a planar tile array comprising a plurality of regions and a plurality of barcoded oligonucleotides, wherein a barcoded oligonucleotide of the tile array comprises at least an amplification primer, a primer-specific barcode, and a regional barcode shared between a first region of the tile array and different among barcoded oligonucleotides of different regions on the tile array;
   (b) translocating the liberated nucleic acids through the pores of the porous cellular support in a direction perpendicular to the porous cellular support substrate under such conditions that the liberated nucleic acids hybridize to at least some of the plurality of barcoded oligonucleotides, thereby generating hybridized cellular nucleic acids;
   (c) amplifying the hybridized cellular nucleic acids to generate a plurality of amplification products therefrom, wherein the amplification products are barcoded using the barcoded oligonucleotides of the tile array, and wherein the regional barcode associates the amplification product with a region of the cell in the cellular sample;
- (d) correlating at least some of the amplification products with the region;
- (e) generating an image of the cellular sample using a computer interface;
- (f) selecting one or more regions of interest in the cellular sample for enrichment using the computer interface;
- (g) providing by computer interface, one or more primers associated with the regions of interest; and
- (h) enriching nucleic acids associated with the region of interest of the cellular sample.

8. A method for spatially resolving protein and/or nucleic acids from a cell of a biological sample, comprising the steps of:
- (a) mounting the biological sample comprising the cell to a first surface, wherein the first surface comprises a porous material;
- (b) hydrating the sample;
- (c) placing the sample in a chamber defined between the first surface and a second surface comprising a tile barcode array, wherein the tile barcode array comprises a plurality of regions and a plurality of barcoded oligonucleotides each comprising an amplification primer, a primer-specific barcode, and a regional barcode common among the barcoded oligonucleotides in a first region of the plurality of regions and different among different regions, wherein the second surface is electrically conductive, and wherein the sample is in direct fluid communication with the first surface and the second surface;
- (d) obtaining positional information regarding the sample relative to the tile barcode array;
- (e) digesting the biological sample to release a plurality of cellular nucleic acid molecules from the cell into the chamber;
- (f) translocating the plurality of cellular nucleic acid molecules inside the chamber, in a direction essentially perpendicular to the first surface toward the second surface;
- (g) hybridizing the plurality of cellular nucleic acid molecules to the barcoded oligonucleotides of the tile barcode array thereby generating a plurality of hybridized nucleic acid molecules, wherein the regional barcode identifies the location of the cell on the first surface;
- (h) sequencing the hybridized nucleic acids;
- (i) correlating the results of the sequencing to the regions within the sample and the first surface from which the cellular nucleic acid molecules originated, using the regional barcode;
- (j) generating an image of the biological sample using a computer interface, and correlating the data generated by sequencing with the regions of the first and second surface on the image;
- (k) selecting one or more regions of interest for enrichment using the computer interface;
- (l) providing by computer interface, one or more primers associated with the regions of interest; and
- (m) enriching nucleic acids associated with the region of interest of the biological sample.

9. The method of claim 8, wherein the tile barcode array is (a) permanently fixed to the second surface; or is (b) releasable from the second surface by endonuclease activity or temperature.

10. The method of claim 8, wherein the plurality of regions comprises at least 3,000 regions.

11. The method of claim 8, wherein the probes comprise one or more of (a) a sequence that allows for quantification of the copy number of sample template and (b) a sequence that allows for enrichment of a specific region of the tile barcode array.

12. The method of claim 8, further comprising contacting the second surface with, one or more of a RNA or DNA dependent DNA polymerase, a ligase, exonuclease, and an endonuclease.

* * * * *